(12) United States Patent
Brandt et al.

(10) Patent No.: US 6,673,107 B1
(45) Date of Patent: Jan. 6, 2004

(54) BIFURCATED STENT AND METHOD OF MAKING

(75) Inventors: Brian D. Brandt, San Jose, CA (US); Joseph R. Callol, San Francisco, CA (US); Hans F. Valencia, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/455,592

(22) Filed: Dec. 6, 1999

(51) Int. Cl.[7] ................................................. A61F 2/06
(52) U.S. Cl. ...................................................... 623/1.35
(58) Field of Search ................................. 623/1.35, 1.1, 623/1.15, 1.16

(56) References Cited

U.S. PATENT DOCUMENTS

| | | | |
|---|---|---|---|
| 2,845,959 | A | 8/1958 | Sidebotham |
| 2,978,787 | A | 4/1961 | Liebig |

(List continued on next page.)

FOREIGN PATENT DOCUMENTS

| | | |
|---|---|---|
| EP | 0 461 791 A1 | 12/1991 |
| EP | 0 466 518 A3 | 1/1992 |
| EP | 0 747 020 A2 | 2/1996 |
| EP | 0 732 088 | 9/1996 |
| EP | 0 804 907 A | 11/1997 |
| EP | 0 897 700 A1 | 2/1999 |
| FR | 2 737 969 A | 2/1997 |
| SU | 1217402 A | 3/1986 |
| SU | 1318235 A1 | 6/1987 |
| SU | 1389778 A2 | 4/1988 |
| SU | 1457921 A1 | 2/1989 |

(List continued on next page.)

OTHER PUBLICATIONS

Mirich, David, M.D., *Percutaneously Placed Endovascular Grafts for Aortic Aneurysms: Feasibility Study, Radiology*, vol. 170, No. 3, Part 2, pp. 1033–1037 (1989).
Chuter, Timothy A.M., BM, BS, et al., *Transfemoral Endovascular Aortic Graft Placement, Journal of Vascular Surgery*, pp. 185–196 (Aug., 1993).
Bard XT Catina Bifurcate Stent (Brochure) (Undated).
Lawrence, David D., Jr., M.D., et al., *Percutaneous Endovascular Graft: Experimental Evaluation, Radiology*, vol. 163, No. 2, pp. 357–360 (1987).
Yoshioka, Tetsuya, et a., *Self–Expanding Endovascular Graft: An Experimental Study in Dogs, Radiology*, vol. 170, pp. 1033–1037 (1989).
Parodi, J.C., M.D., et al., *Transfemoral Intraluminal Graft Implantation for Abdominal Aortic Aneuyrsms, Annals of Vascular Surgery*, vol. 5, No. 6, pp. 491–499 (1991).

*Primary Examiner*—Corrine McDermott
*Assistant Examiner*—A. Stewart
(74) *Attorney, Agent, or Firm*—Fulwider Patton Lee & Utecht, LLP

(57) ABSTRACT

A Y-shaped stent, or bifurcated stent, for stenting bifurcated vessels consists of a first generally cylindrical distal branch defining a first flow path for fluid flow, and a second generally cylindrical distal branch defining a second flow path for fluid flow. The first and second distal branches are interconnected by one or more bending elements at a carina junction, each of the bending elements being flexible such that the first and second distal branches are capable of pivoting about the bending elements at the carina junction, thus defining an angle of varying degree. A generally cylindrical proximal branch defines a third flow path for fluid flow. The proximal branch is attached to the first and second distal branches proximate the carina junction such that the first and second distal branches and the proximal branch are in communication with each other.

15 Claims, 18 Drawing Sheets

U.S. PATENT DOCUMENTS

| | | |
|---|---|---|
| 2,990,605 A | 7/1961 | Demsyk |
| 3,029,819 A | 4/1962 | Starks |
| 3,096,560 A | 7/1963 | Liebig |
| 3,142,067 A | 7/1964 | Liebig |
| 3,657,744 A | 4/1972 | Ersek |
| 3,908,662 A | 9/1975 | Razgulov et al. |
| 3,945,052 A | 3/1976 | Liebig |
| 4,041,931 A | 8/1977 | Elliott et al. |
| 4,047,252 A | 9/1977 | Liebig et al. |
| 4,061,134 A | 12/1977 | Samuels et al. |
| 4,108,161 A | 8/1978 | Samuels et al. |
| 4,140,126 A | 2/1979 | Choudhury |
| 4,193,137 A | 3/1980 | Heck |
| 4,202,349 A | 5/1980 | Jones |
| 4,214,587 A | 7/1980 | Sakura, Jr. |
| 4,517,687 A | 5/1985 | Liebig et al. |
| 4,560,374 A | 12/1985 | Hammerslag |
| 4,562,596 A | 1/1986 | Kornberg |
| 4,577,631 A | 3/1986 | Kreamer |
| 4,617,932 A | 10/1986 | Kornberg |
| 4,652,263 A | 3/1987 | Herweck et al. |
| 4,693,249 A | 9/1987 | Schenck et al. |
| 4,728,328 A | 3/1988 | Hughes et al. |
| 4,732,152 A | 3/1988 | Wallsten et al. |
| 4,739,762 A | 4/1988 | Palmaz |
| 4,787,899 A | 11/1988 | Lazarus |
| 4,793,348 A | 12/1988 | Palmaz |
| 4,795,458 A | 1/1989 | Regan |
| 4,795,465 A | 1/1989 | Marten |
| 4,830,003 A | 5/1989 | Wolff et al. |
| 4,872,874 A | 10/1989 | Taheri |
| 4,878,906 A | 11/1989 | Lindemann et al. |
| 4,892,539 A | 1/1990 | Koch |
| 4,969,890 A | 11/1990 | Sugita et al. |
| 4,969,896 A | 11/1990 | Shors |
| 4,994,071 A | 2/1991 | MacGregor |
| 5,026,377 A | 6/1991 | Burton et al. |
| 5,047,050 A | 9/1991 | Arpesani |
| 5,104,399 A | 4/1992 | Lazarus |
| 5,108,424 A | 4/1992 | Hoffman, Jr. et al. |
| 5,127,919 A | 7/1992 | Ibrahim et al. |
| 5,156,619 A | 10/1992 | Ehrenfeld |
| 5,178,630 A | 1/1993 | Schmitt |
| 5,178,634 A | 1/1993 | Ramos-Martinez |
| 5,197,976 A | 3/1993 | Herweck et al. |
| 5,197,977 A | 3/1993 | Hoffman, Jr. et al. |
| 5,304,220 A | 4/1994 | Maginot |
| 5,316,023 A | 5/1994 | Palmaz et al. |
| 5,360,443 A | 11/1994 | Barone et al. |
| 5,443,497 A | 8/1995 | Venbrux |
| 5,443,498 A | 8/1995 | Fontaine |
| 5,456,712 A | 10/1995 | Maginot |
| 5,514,154 A * | 5/1996 | Lau et al. .................. 606/195 |
| 5,522,880 A | 6/1996 | Barone et al. |
| 5,527,355 A | 6/1996 | Ahn |
| 5,562,724 A | 10/1996 | Vorwerk et al. |
| D376,011 S | 11/1996 | Nunokawa |
| 5,571,170 A | 11/1996 | Palmaz et al. |
| 5,571,171 A | 11/1996 | Barone et al. |
| 5,571,173 A | 11/1996 | Parodi |
| 5,575,817 A | 11/1996 | Martin |
| 5,578,072 A | 11/1996 | Barone et al. |
| 5,591,228 A | 1/1997 | Edoga |
| 5,591,229 A | 1/1997 | Parodi |
| 5,603,721 A | 2/1997 | Lau et al. |
| 5,609,627 A | 3/1997 | Goicoechea et al. |
| 5,613,980 A | 3/1997 | Chauhan |
| 5,617,878 A | 4/1997 | Taheri |
| 5,632,763 A | 5/1997 | Glastra |
| 5,639,278 A | 6/1997 | Dereume et al. |
| 5,643,340 A | 7/1997 | Nunokawa |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,452 A | 11/1997 | Barone et al. |
| 5,683,453 A | 11/1997 | Palmaz |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,709,713 A | 1/1998 | Evans et al. |
| 5,713,917 A | 2/1998 | Leonhardt et al. |
| 5,718,724 A | 2/1998 | Goicoechea et al. |
| 5,720,735 A | 2/1998 | Dorros |
| 5,749,825 A | 5/1998 | Fischell et al. |
| 5,755,734 A | 5/1998 | Richter et al. |
| 5,755,735 A | 5/1998 | Richter et al. |
| 5,755,771 A | 5/1998 | Penn et al. |
| 5,776,180 A | 7/1998 | Goicoechea et al. |
| 5,782,906 A | 7/1998 | Marshall et al. |
| 5,800,508 A | 9/1998 | Goicoechea et al. |
| 5,800,520 A | 9/1998 | Fogarty et al. |
| 5,827,320 A | 10/1998 | Richter et al. |
| 5,893,887 A | 4/1999 | Jayaraman |
| 5,895,407 A | 4/1999 | Jayaraman |
| 5,916,234 A | 6/1999 | Lam |
| 5,916,263 A | 6/1999 | Goicoechea et al. |
| 5,919,225 A | 7/1999 | Lau et al. |
| 5,921,995 A | 7/1999 | Kleshinski |
| 5,938,696 A | 8/1999 | Goicoechea et al. |
| 5,954,693 A | 9/1999 | Barry |
| 5,972,017 A | 10/1999 | Berg |
| 5,976,155 A | 11/1999 | Foreman et al. |
| 6,030,413 A | 2/2000 | Lazarus |
| 6,030,414 A | 2/2000 | Taheri |
| 6,030,415 A | 2/2000 | Chuter |
| 6,033,434 A | 3/2000 | Borghi |
| 6,033,435 A | 3/2000 | Penn et al. |
| 6,039,754 A | 3/2000 | Caro |
| 6,048,361 A | 4/2000 | Von Oepen |
| 6,051,020 A | 4/2000 | Goicechea et al. |
| 6,322,587 B1 * | 11/2001 | Quiachon et al. .......... 623/1.23 |

FOREIGN PATENT DOCUMENTS

| | | |
|---|---|---|
| SU | 1482714 A2 | 5/1989 |
| WO | WO 95/16406 | 6/1995 |
| WO | WO 95/21592 | 8/1995 |
| WO | WO 96/23455 | 8/1996 |
| WO | WO 96/24306 | 8/1996 |
| WO | WO 96/24308 | 8/1996 |
| WO | WO 96/34580 A | 11/1996 |
| WO | WO 96/34580 | 11/1996 |
| WO | WO 97/07752 | 3/1997 |
| WO | WO 97/15345 | 5/1997 |
| WO | WO 97/16217 | 5/1997 |
| WO | WO 98/19628 | 10/1997 |
| WO | WO 97/41803 | 11/1997 |
| WO | WO 97/45073 | 12/1997 |
| WO | WO 98/36709 | 2/1998 |
| WO | WO 99/04726 | 2/1999 |
| WO | WO 99/58084 | 11/1999 |

* cited by examiner

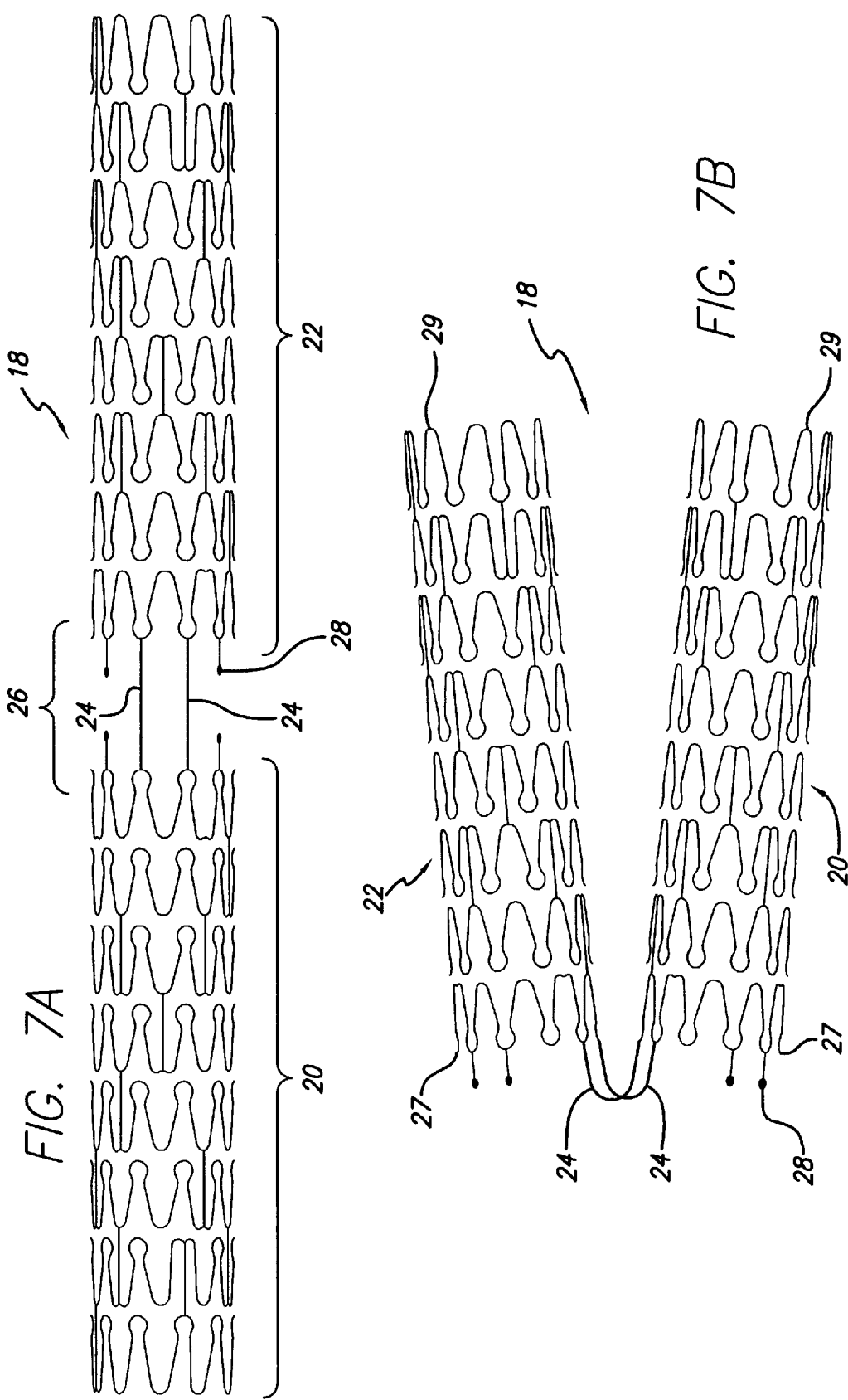

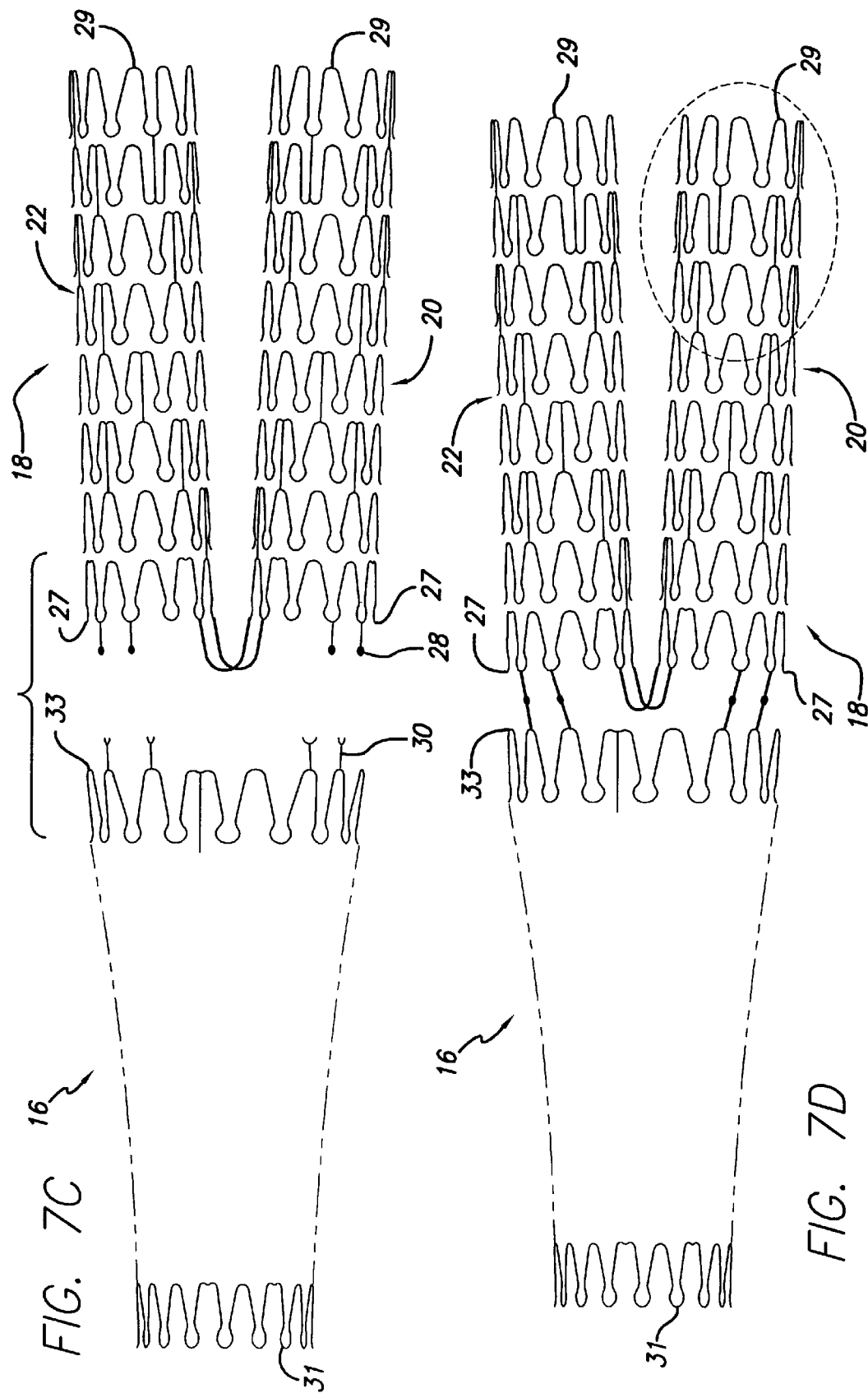

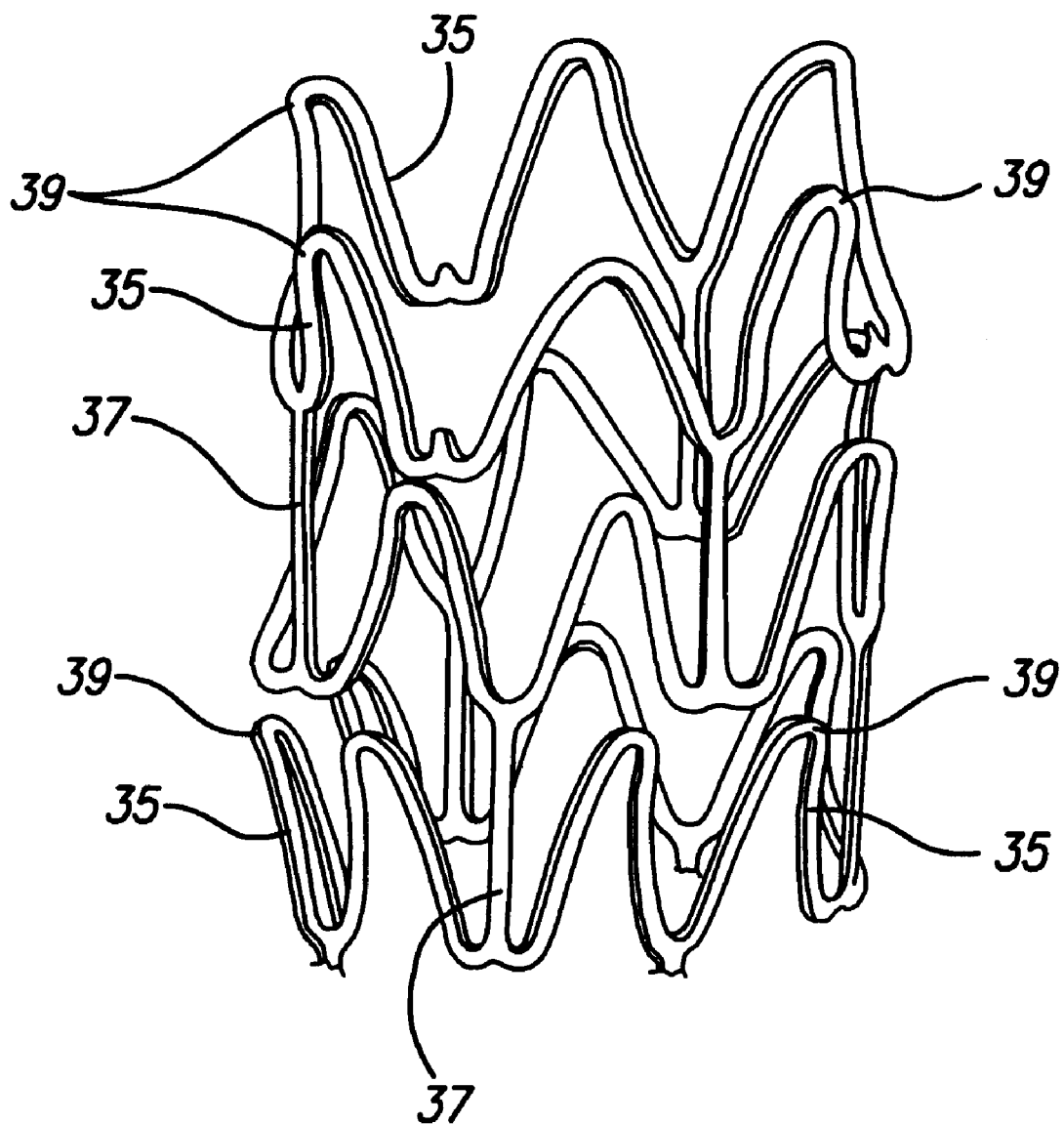

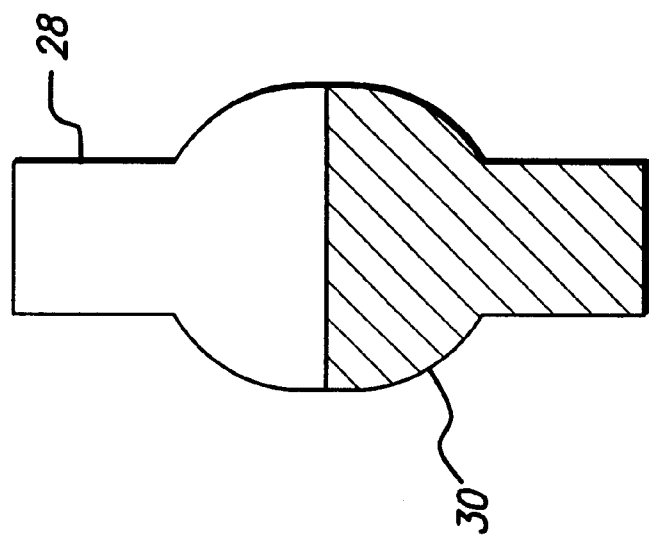
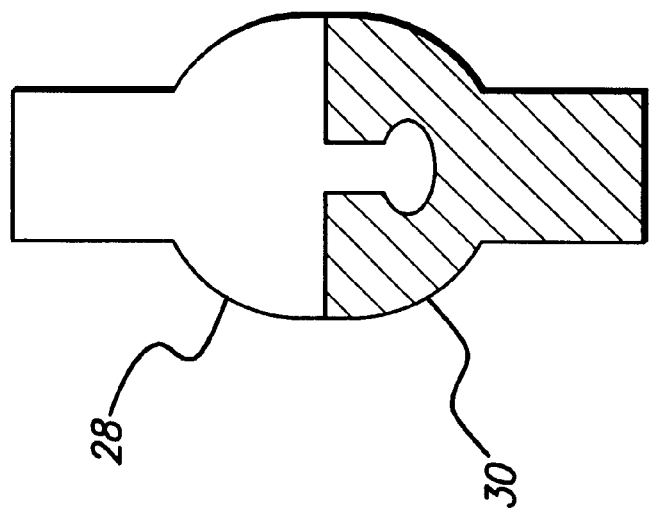
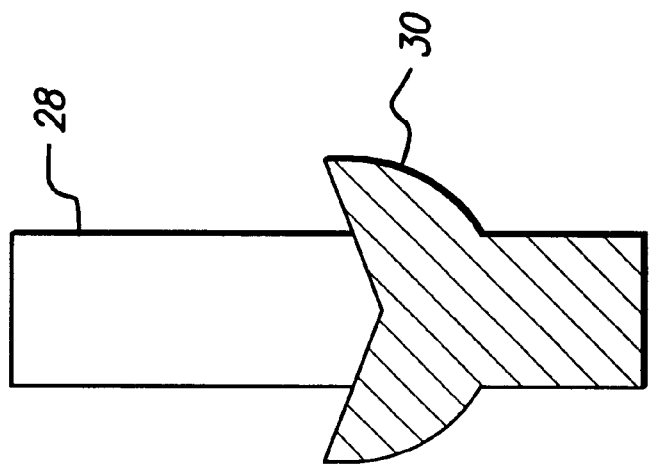

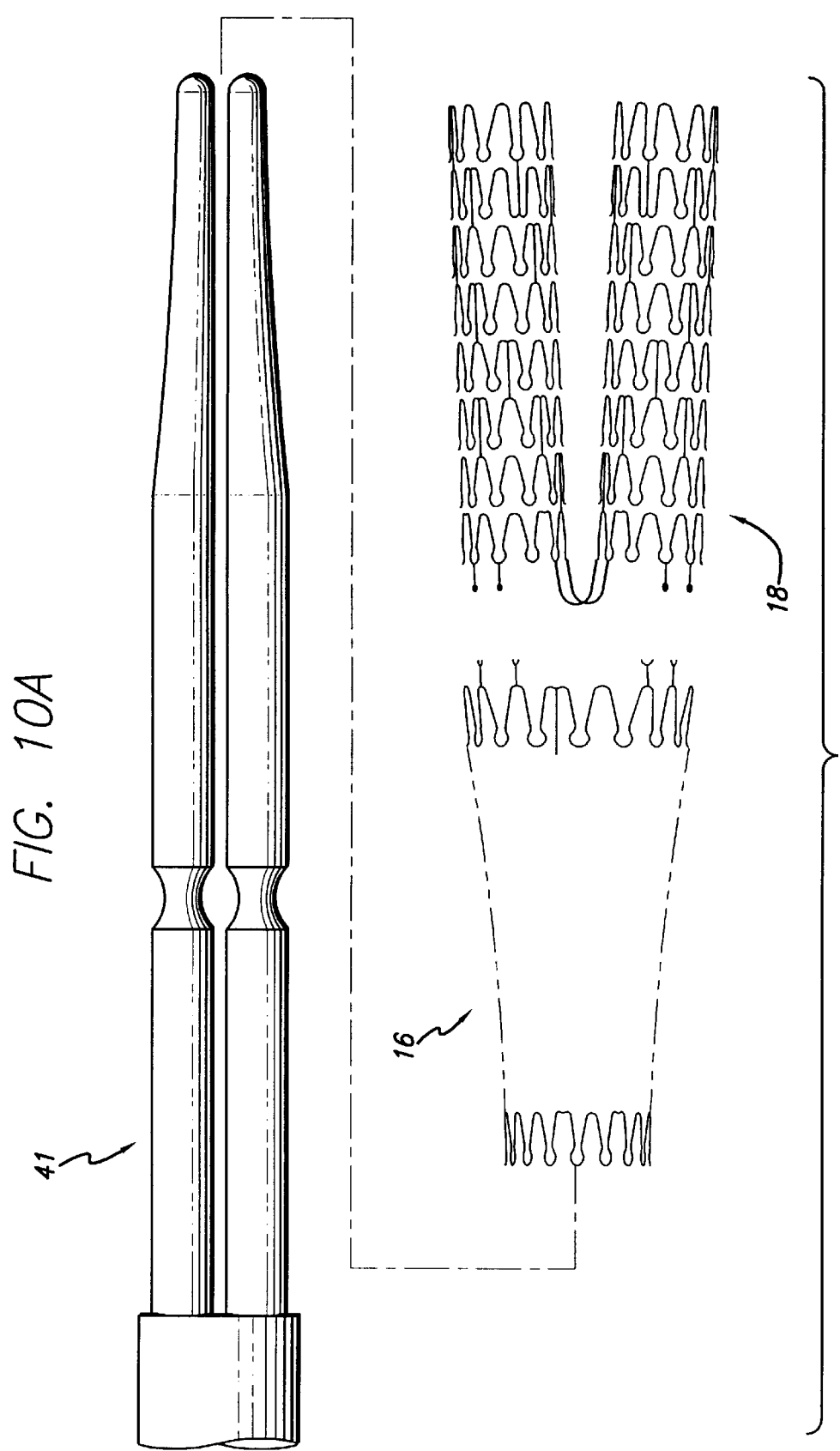

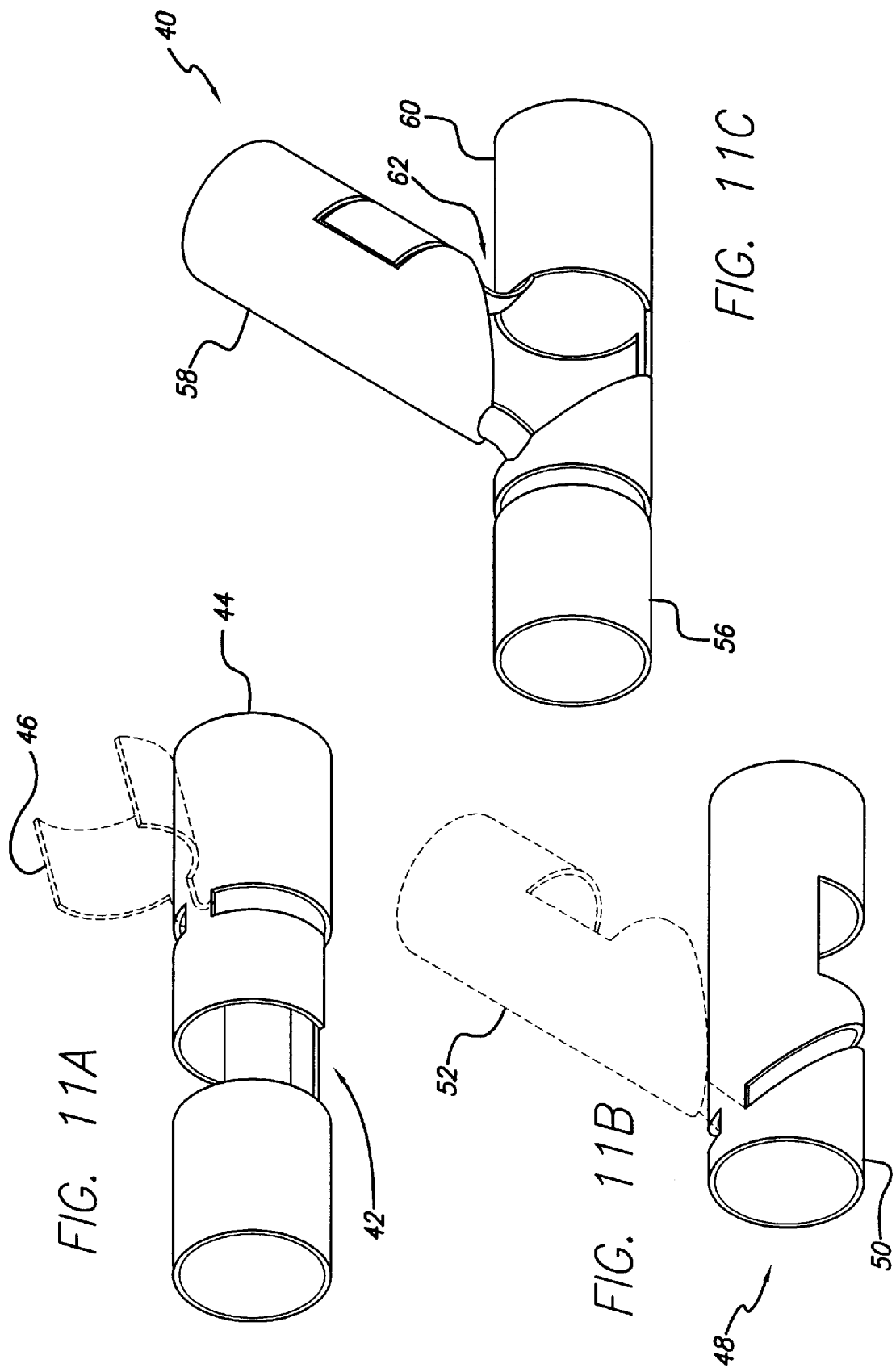

BIFURCATED STENT AND METHOD OF MAKING

BACKGROUND OF THE INVENTION

The invention relates generally to a stent for use at a bifurcation and, more particularly, a Y-shaped intraluminal vascular stent for repairing bifurcations, the aorto-ostium, and bifurcated blood vessels that are diseased.

Stents are conventionally used for revascularization or re-establishment of blood flow through vessels. Stents are generally hollow and cylindrical in shape and have terminal ends that are generally perpendicular to their longitudinal axes. In use, the conventional stent is positioned at the diseased area of a vessel and, after placement, the stent provides an unobstructed pathway for blood flow.

Re-establishing blood flow through diseased vessels at a bifurcation is particularly challenging since the stent must overlay the entire diseased area at the bifurcation, yet not itself compromise blood flow. Therefore, the stent must, without compromising blood flow, provide adequate coverage by overlaying the entire circumference of the ostium to a diseased portion and extend to a point within and beyond the diseased portion. When the stent does not provide adequate coverage, then potential failure can occur by allowing disease to prolapse into the vessel lumen. When the stent overlays the entire circumference of the ostium to the diseased portion, yet extends into the junction comprising the bifurcation, the diseased area is repaired, but blood flow may be compromised in other portions of the bifurcation. Unapposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlying the entire circumference of the ostium extends back into the aorta, creating problems, including those for repeat catheter access to the vessel involved in further interventional procedures.

Conventional stents are designed to re-establish blood flow in vessels that are removed from bifurcations and, since conventional stents generally terminate at right angles to their longitudinal axes, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extends so far as to completely cover the path of blood flow in a side branch. The conventional stent might alternatively be placed proximal to, but not entirely overlaying the circumference of the ostium to the diseased portion. Such a position of the conventional stent can result in a bifurcation that is not completely repaired or can compromise blood flow into areas or origins requiring blood for proper function.

The only conceivable situation in which the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result in the right-angled terminal ends of the conventional stent overlying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, may be employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting such stents has presented numerous problems. For example, a conventional stent is implanted in the main vessel so that a portion of the stent is across the side branch, so that stenting of the side branch must occur through the main-vessel stent struts. In this method, commonly referred to in the art as the "monoclonal antibody" approach, the main-vessel stent struts must be spread apart to form an opening to the side-branch vessel and then a catheter with a stent is delivered through the opening. The cell to be spread apart must be randomly and blindly selected by recrossing the deployed stent with a wire. The drawback with this approach is there is no way to determine or guarantee that the main-vessel stent struts are properly oriented with respect to the side branch or that the appropriate cell has been selected by the wire for dilatation. The aperture created often does not provide a clear opening and creates a major distortion in the surrounding stent struts. The drawback with this approach is that there is no way to tell if the main-vessel stent struts have been properly oriented and spread apart to provide a clear opening for stenting the side-branch vessel.

In another prior art method for treating bifurcated vessels, commonly referred to as the "Culotte technique," the side-branch vessel is first stented so that the stent protrudes into the main vessel. A dilatation is then performed in the main vessel to open and stretch the stent struts extending across the lumen from the side-branch vessel. Thereafter, the main-vessel stent is implanted so that its proximal end overlaps with the side-branch vessel. One of the drawbacks of this approach is that the orientation of the stent elements protruding from the side-branch vessel into the main vessel is completely random. Furthermore the deployed stent must be recrossed with a wire blindly and arbitrarily selecting a particular stent cell. When dilating the main-vessel stent, stretching the stent struts is therefore random, leaving the possibility of restricted access, incomplete lumen dilatation, and major stent distortion. Furthermore, this technique is rapidly falling into disfavor due to the excess metal that must be placed within the parent or proximal vessel.

In another prior art device and method of implanting stents, a "T" stent procedure includes implanting a stent in the side-branch ostium of the bifurcation followed by stenting the main vessel across the side-branch ostium. In another prior art procedure, known as "kissing" stents, a stent is implanted in the main vessel with a side-branch stent partially extending into the main vessel creating a double-barrelled lumen of the two stents in the main vessel proximate the bifurcation. Another prior art approach includes a so-called "trouser legs and seat" approach, which includes implanting three stents, one stent in the side-branch vessel, a second stent in a distal portion of the main vessel, and a third stent, or a proximal stent, in the main vessel proximate the bifurcation.

All of the foregoing stent deployment assemblies suffer from the same problems and limitations. Typically, there are uncovered intimal surface segments on the main vessel and side-branch vessels between the stented segments. An uncovered flap or fold in the intima or plaque will invite a "snowplow" effect, representing a substantial risk for subacute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use, making successful placement nearly impossible. Further, even where placement has been successful, the side-branch vessel can be "jailed" or covered so that there is impaired access to the stented area for subsequent intervention.

Previous attempts have been made to produce bifurcated stents, or Y-shaped stents, for treating arterial bifurcations. Typically, these prior art stents are difficult to manufacture. Moreover, these prior art stents are often bulky making them difficult to deliver and precisely place at the carina of the vessel. Moreover, these stents often lack sufficient scaffolding at the carina and other areas to properly cover existing disease within the vessel. The present invention solves these and other problems as will be shown.

What has been needed and heretofore unavailable is an improved Y-shaped stent that can be used to effectively treat arterial bifurcations. It is also desirable that such a Y-shaped stent be easy to use and precisely place, relatively inexpensive to manufacture, and constructed from materials that are common in the industry today. The present invention satisfies these needs.

SUMMARY OF THE INVENTION

The present invention is directed to an improved Y-shaped stent design for repairing a main vessel and side-branch vessel forming a bifurcation. The stent may easily be placed with precision at a bifurcation to effectively treat a diseased area. Moreover, the manufacturing process has been simplified.

In one aspect of the invention there is provided a longitudinally flexible Y-shaped stent for implanting in a bifurcated body lumen that includes a first generally cylindrical distal branch defining a first flow path for fluid flow and second generally cylindrical distal branch defining a second flow path for fluid flow. The first and second distal branches are interconnected by one or more bending elements at a carina junction. Each of the bending elements are flexible such that the first and second distal branches are capable of pivoting about the bending elements at the carina junction, thus defining an angle of varying degree such that the carina junction extends proximal the proximal end of the first and second distal branches.

The Y-shaped stent further includes a generally cylindrical proximal branch defining a third flow path for fluid flow. The proximal branch is attached to the first and second distal branches proximal the carina junction such that the first and second distal branches and the proximal branch are in communication with each other. During delivery of the Y-shaped stent in the bifurcated lumen, the carina junction comes into apposition with the carina of the body lumen so that the Y-shaped stent can no longer be advanced distally, which facilitates precise placement of the Y-shaped stent in the bifurcated lumen.

In another aspect of the invention there is provided a longitudinally flexible Y-shaped stent for implanting in a bifurcated body lumen and expandable from contracted condition to an expanded condition. The Y-shaped stent includes a plurality of adjacent cylindrical elements each having a circumference extending around a longitudinal stent axis and each element being substantially independently expandable in the radial direction, the cylindrical elements being arranged in alignment along the longitudinal stent axis. The cylindrical elements are formed in a generally serpentine wave pattern transverse to the longitudinal axis and contain a plurality of alternating peaks and valleys. The peaks on each of the cylindrical elements are substantially aligned in phase along the longitudinal stent axis. At least one interconnecting member extends between adjacent cylindrical elements and connects them to one another to form the longitudinally flexible Y-shaped stent.

The Y-shaped stent has a proximal end and a distal end in communication with each other, the proximal end including a generally cylindrical proximal branch and the distal end including a first generally cylindrical distal branch and a second generally cylindrical distal branch. The first and second distal branches and the proximal branch are in communication with each other.

In yet another aspect of the invention there is provided a longitudinally flexible Y-shaped stent for implanting in a bifurcated body lumen, including a plurality of cylindrical elements that are independently expandable in the radial direction and that are interconnected so as to be generally aligned on a common longitudinal axis. The Y-shaped stent further includes a plurality of connecting elements for interconnecting the cylindrical elements. The connecting elements are configured to interconnect only the cylindrical elements that are adjacent to each other. There is an outer wall surface on the cylindrical elements, the outer wall surface being smooth prior to expansion of the Y-shaped stent and forming a plurality of outwardly projecting edges that form as the stent is expanded radially outwardly from a first diameter to a second, enlarged diameter.

Similarly, this Y-shaped stent also has a proximal end and a distal end in communication with each other, the proximal end including a generally cylindrical proximal branch and the distal end including a first generally cylindrical distal branch and a second generally cylindrical distal branch. The first and second distal branches and the proximal branch are in communication with each other.

In a still further aspect of the invention there is provided a method of making an expandable metal Y-shaped stent, including the step of forming a proximal stent section out of a first metal tube and a distal stent section out of a second metal tube, the distal stent section having a first distal branch and a second distal branch. The first distal branch and the second distal branch are connected by bending elements, thereby forming a carina junction. Male struts and female struts are cut into the first tube and the second tube such that decreasing the angle between the distal branches serves to cause the male and female struts cut into the second tube to assume a position to facilitate attachment.

In another aspect of the invention there is provided a longitudinally flexible Y-shaped stent for implanting in a bifurcated body lumen, including a first stent section having a first main portion and a first hinged portion, the first hinged portion being hingedly attached to the first main portion such that the first stent section has an open configuration and a closed configuration. A second stent section has a second main portion and a second hinged portion, the second hinged portion being hingedly attached to the second main portion such that the second stent section has an open configuration and a closed configuration.

The first stent section may be mated with the second stent section while the first stent section and the second stent section are in open configurations. Once mated, the first stent section together with the second stent section create a combination having a proximal end and a distal end in communication with each other. The proximal end includes a generally cylindrical proximal branch, and the distal end includes a first generally cylindrical distal branch and a second generally cylindrical distal branch. The first and second distal branches and the proximal branch are in communication with each other.

In another aspect there is provided a method of making an expandable metal Y-shaped stent, including the step of forming a first stent section out of a first metal tube and a second stent section out of a second metal tube. The first stent section has a first main portion and a first hinged portion hingedly attached to the first main portion such that the first stent section has an open configuration and a closed configuration. The second stent section has a second main portion and a second hinged portion hingedly attached to the second main portion such that the second stent section has an open configuration and a closed configuration.

Other features and advantages of the present invention will become more apparent from the following detailed description of the invention, when taken in conjunction with the accompanying exemplary drawings.

BRIEF DESCRIPTION OF THE DRAWINGS

FIG. 7A depicts a perspective view of a distal stent section of one embodiment of the Y-shaped stent of the present invention.

FIG. 7B is a perspective view of the distal stent section of FIG. 7A being bent at a carina junction.

FIG. 7C depicts a perspective view of the proximal and distal stent sections of FIGS. 7A and 7B.

FIG. 7D depicts a perspective view of the proximal and distal stent sections of FIGS. 7A and 7B in assembled relation.

FIG. 7E depicts a perspective view of the portion of the stent indicated by the circle in FIG. 7D after it is fully expanded showing the outwardly projecting edges of the outer wall surface.

FIG. 9B is an elevational view, in section, of a male and a female strut in a second "fork," or "duck," configuration.

FIG. 9C is an elevational view, in section, of a male and a female strut in a "locking butt," or "ball and socket," configuration.

FIG. 9D is an elevational view, in section, of a male and a female strut in a "butt" configuration.

FIG. 10A is a perspective view of the welding mandrel before the Y-shaped stent is mounted thereon for welding.

FIG. 11A is a perspective schematic view of a first stent section of another embodiment of the Y-shaped stent of the present invention.

FIG. 11B is a perspective schematic view of a second stent section.

FIG. 11C is a perspective view of the Y-shaped stent represented in FIGS. 11A and 11B in assembled relation.

DETAILED DESCRIPTION OF THE PREFERRED EMBODIMENTS

Figure 1:
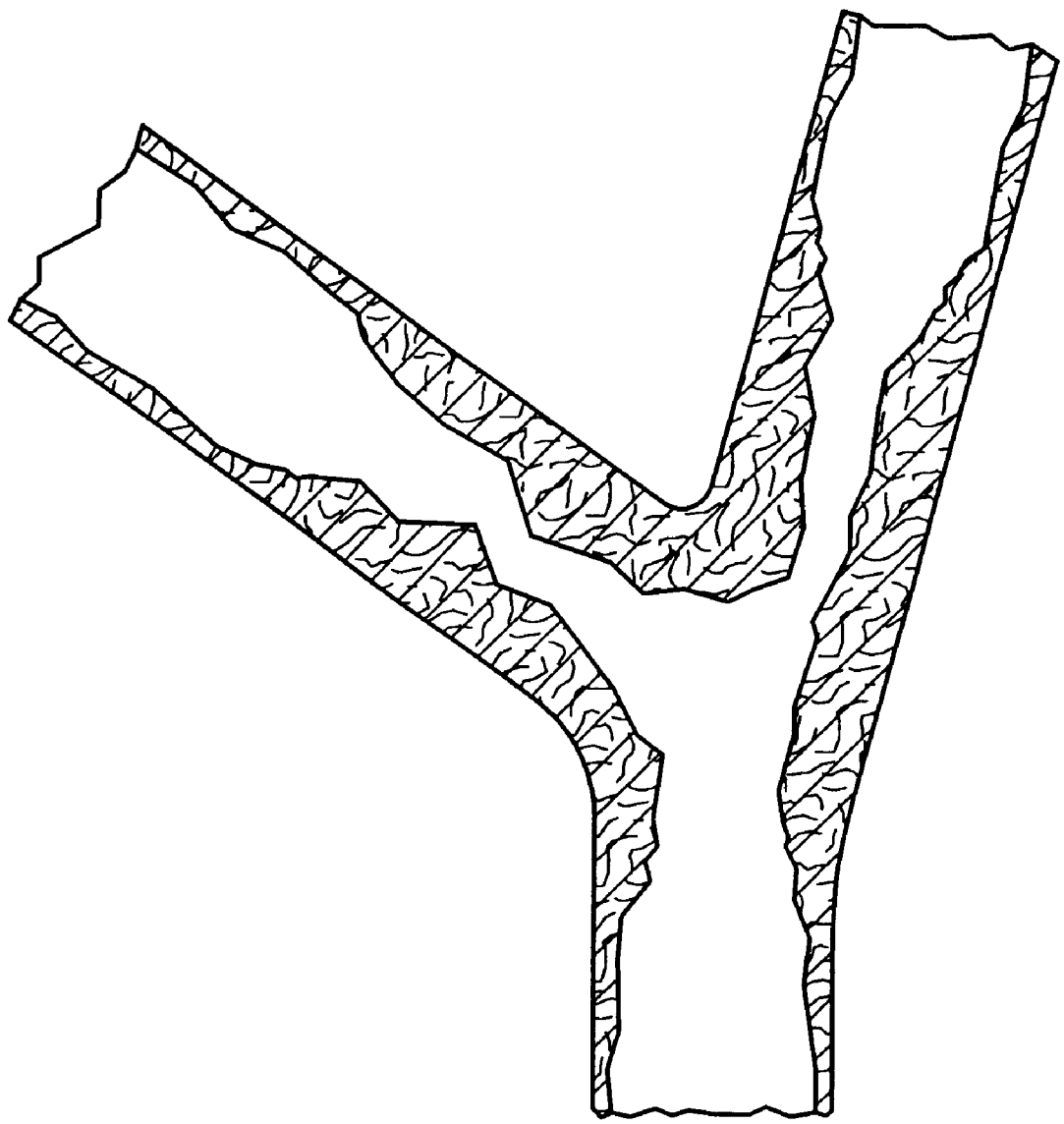
FIG. 1 is a sectional view of a diseased arterial bifurcation.

As shown in the exemplary drawings, the present invention is embodied in a Y-shaped stent for treating bifurcated vessels. Like reference numerals indicate like or corresponding elements among the figures.

As explained above, it would be desirable to be able to effectively treat bifurcated lesions with a single stent that treats all of the disease without compromising blood flow. It would also be desirable to achieve a method of manufacturing such a stent with a minimum of difficulty and expense.

In accordance with the present invention, a Y-shaped stent is contemplated for treating bifurcations in, for example, the coronary arteries, veins, arteries, and other vessels in the body. Referring to FIG. 1, an arterial bifurcation is a site within the vasculature of a body where an artery divides into two vessel passages. FIG. 1 also illustrates how plaque can build up on the artery walls creating a narrowing known as stenosis. The stenosis can be dilated using a balloon catheter to compress the plaque against the vessel wall in a procedure known as percutaneous transluminal coronary angioplasty (PTCA).

Figure 2:
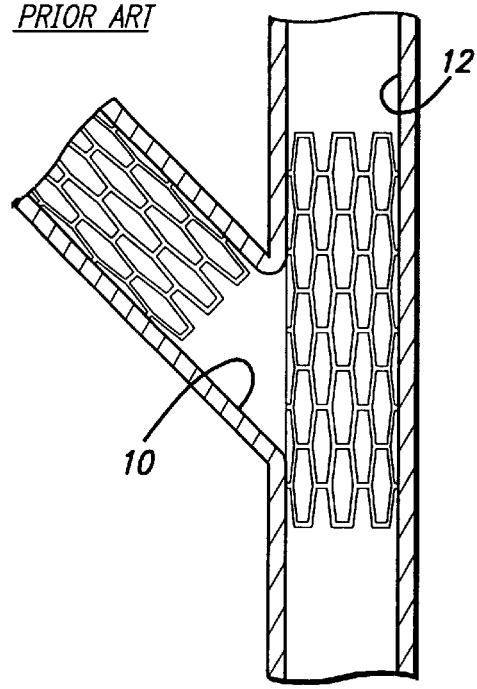
FIG. 2 is an elevational view of a bifurcation in which a prior art "T" stent is in a side-branch ostium followed by the stenting of the main vessel across the branch ostium.

Prior art attempts at treating bifurcations with intravascular stents have proved less than satisfactory. For example, FIGS. 2–5 depict prior art devices which include multiple stents being implanted in both the main vessel and a side-branch vessel. In FIG. 2, a prior art "T" stent is implanted such that a first stent is implanted in side branch 10 near the ostium of the bifurcation, and a second stent is implanted in main vessel 12, across the side-branch ostium. With this approach, portions of the side-branch vessel are left uncovered, and blood flow to the side-branch vessel must necessarily pass through the main-vessel stent, causing possible obstructions or thrombosis.

Figure 3:
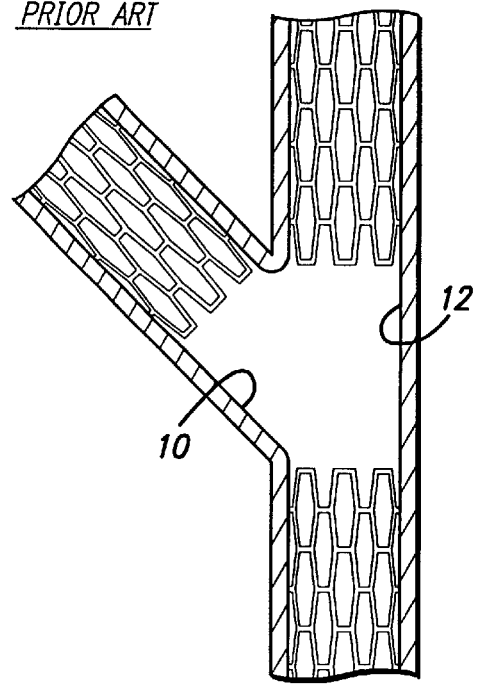
FIG. 3 is an elevational view of a bifurcation in which "touching" prior art stents are depicted in which one stent is implanted in the side branch, and a second stent is implanted in a portion of the main vessel proximate the branch stent, with interrupted placement of a third stent in the main vessel.
Figure 4:
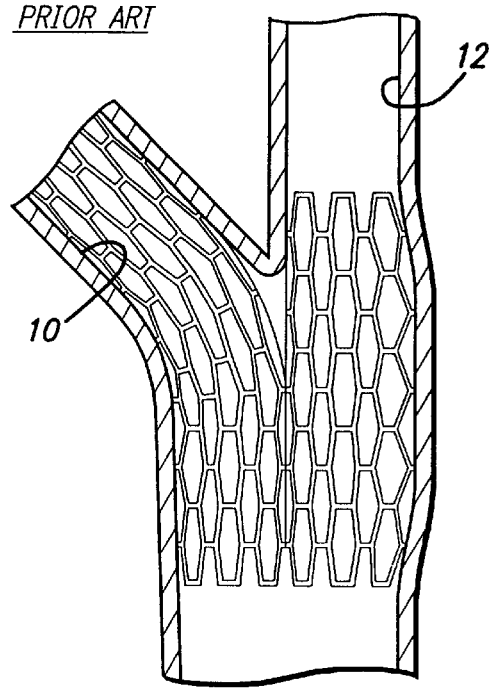
FIG. 4 is an elevational view of a bifurcation depicting "kissing" stents where a portion of one stent is implanted in both the side-branch and the main vessel and is adjacent to a second stent implanted in the main vessel creating a double-barreled lumen in the main vessel proximate the bifurcation.
Figure 5:
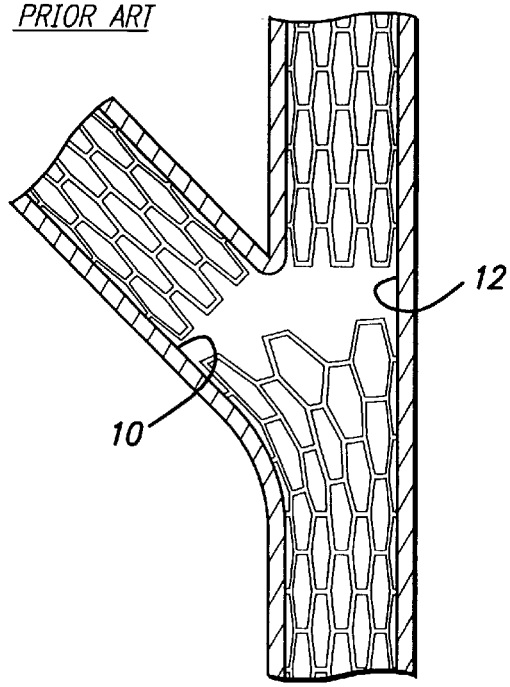
FIG. 5 is an elevational view of a prior art "trouser legs and seat" stenting approach depicting one stent implanted in the side-branch vessel, a second stent implanted in a portion of the main vessel, and a close deployment of a third stent proximate the bifurcation, leaving a small gap between the three stents of an uncovered luminal area.

Referring to FIG. 3, three prior art stents are required to stent the bifurcation. In FIG. 4, the prior art method includes implanting two stents side by side, such that one stent extends into side-branch vessel 10 and main vessel 12, and the second stent is implanted in the main vessel. This results in a double-barreled lumen which can present problems such as thrombosis, and turbulence in blood flow. Referring to the FIG. 5 prior art device, a first stent is implanted in the side-branch vessel, a second stent is implanted in a portion of the main vessel, and a third stent is implanted proximate the bifurcation, thereby leaving a small gap between the stents and an uncovered luminal area.

Figure 6A:
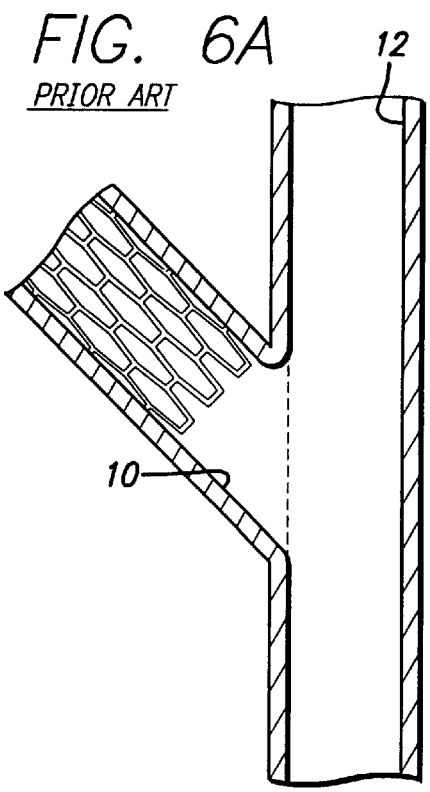
FIG. 6A is an elevational view of a bifurcation in which a prior art stent is implanted in the side-branch vessel.
Figure 6B:
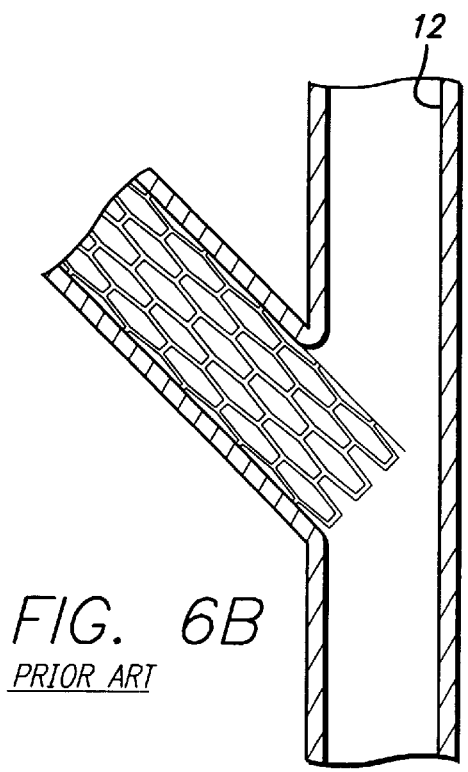
FIG. 6B is an elevational view of a bifurcation in which a prior art stent is implanted in the side-branch vessel, with the proximal end of the stent extending into the main vessel.

Referring now to FIGS. 6A and 6B, a prior art stent deployed in side-branch vessel 10 will leave a portion of the side-branch vessel exposed, or as depicted in FIG. 5B, a portion of the stent will extend into main-vessel 12.

All of the prior art devices depicted in FIGS. 2–6B have various drawbacks with respect to treating bifurcated vessels. These drawbacks have been solved by the present invention.

In one embodiment of the present invention, as depicted in FIGS. 7A–7D, bifurcated stent, or Y-shaped stent 14, includes proximal stent section 16 and distal stent section 18. The distal stent section (FIG. 7A) includes first generally cylindrical distal branch 20 defining a first flow path for fluid flow and second generally cylindrical distal branch 22 defining a second flow path for fluid flow. The first add second distal branches are interconnected by one or more bending elements 24 at carina junction 26. Each of the bending elements are flexible such that the first 20 and second 22 distal branches are capable of pivoting about the bending elements 24 at the carina junction 26, as shown in FIG. 7B, thereby defining a proximal end 27 and distal end 29 of each distal branch. When the first and second distal branches 20, 22 pivot about the bending elements 24 at the carina junction 26, the carina junction is proximal the proximal end 27 of each distal branch. The proximal stent section 16 consists of generally cylindrical proximal branch 16 having a proximal end 31 and distal end 33 and defining a third flow path for fluid flow (FIG. 7C). The proximal branch is attached to the first and second distal branches proximal the carina junction such that the first and second distal branches and the proximal branch are in communication with each other. Preferably, the diameter of the proximal branch is matched to be approximately equal to the sum of the diameters of the distal branches, as illustrated in FIG. 7D. Thus, the proximal branch is designed to accommodate two balloons simultaneously, i.e., a "hugging balloon" technique, or one balloon and the proximal section of a second balloon simultaneously, i.e., a "kissing balloon" technique.

In one embodiment, Y-shaped stent 14 is expandable from a first smaller diameter for delivery in a body lumen to a second expanded diameter by plastically deforming the Y-shaped stent beyond the elastic limits of the material forming the stent. In another embodiment, the Y-shaped stent is formed from a self-expanding material so that the stent expands from a first smaller diameter for delivery through a body lumen to a second implanted diameter in the body lumen. The Y-shaped stent may be formed of a biocompatible material selected from the group of materials including stainless steel, tantalum, nickel-titanium and its alloys, titanium and its alloys, platinum-iridium, chromium-cobalt, palladium-platinum-nickel, tantalum-titanium, platinum, and thermoplastic polymers. The use of other suitable materials to form the Y-shaped stent is contemplated as well.

In another embodiment illustrated in FIG. 7E, the Y-shaped stent 14 includes a plurality of cylindrical elements 35 that are independently expandable in the radial direction and which are interconnected so as to be generally aligned on a common longitudinal axis. The Y-shaped stent 14 further includes a plurality of connecting elements 37 for interconnecting the cylindrical elements 35. The connecting elements 37 are configured to interconnect only the cylindrical elements 35 that are adjacent to each other. There is a outer wall surface on the cylindrical elements, the outer wall surface being smooth prior to expansion of the Y-shaped stent and forming a plurality of outwardly edges 39 that form as the stent is expanded radially outwardly from a first diameter to a second, enlarged diameter.

Figure 8A:
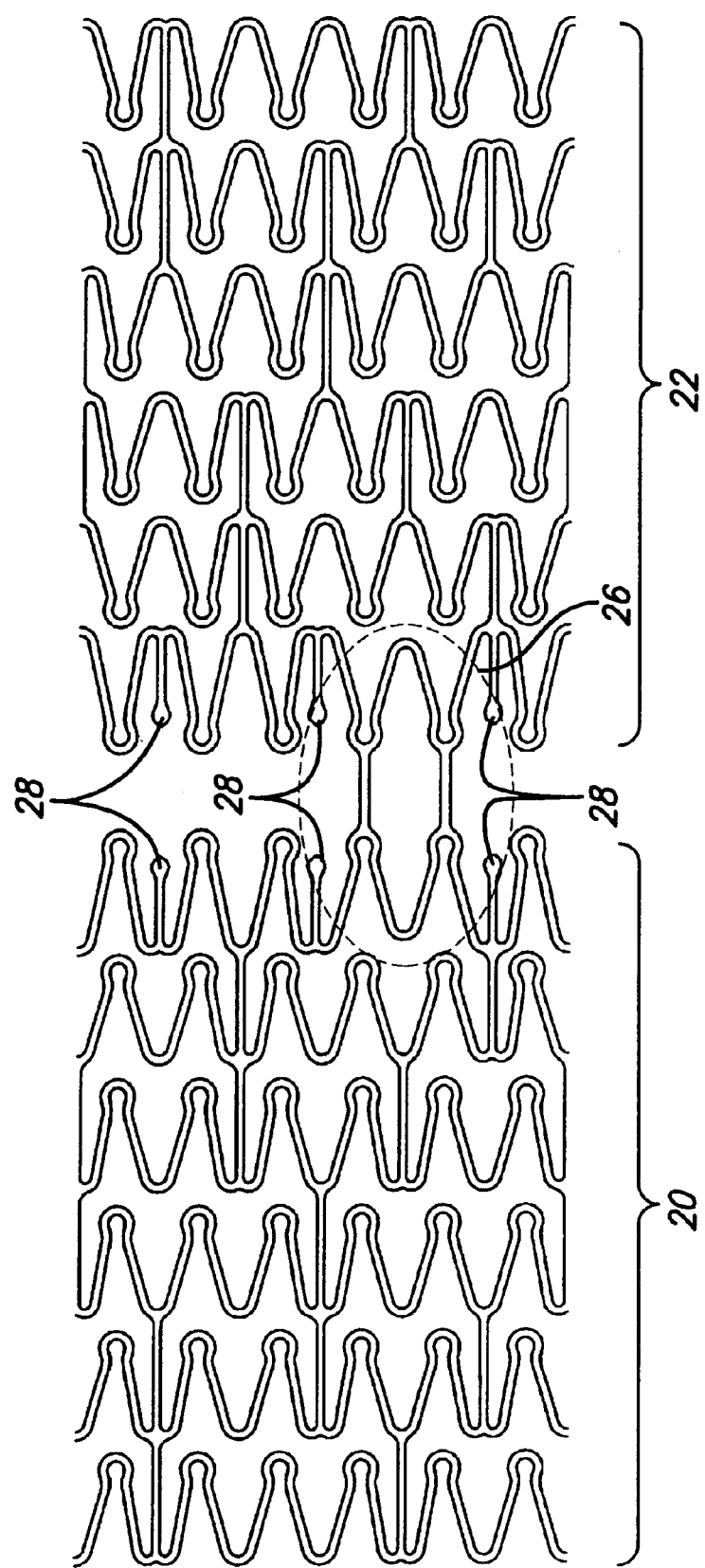
FIG. 8A is a plan view of the distal stent section carina junction and surrounding area of one embodiment of the Y-shaped stent of the present invention.
Figure 8B:
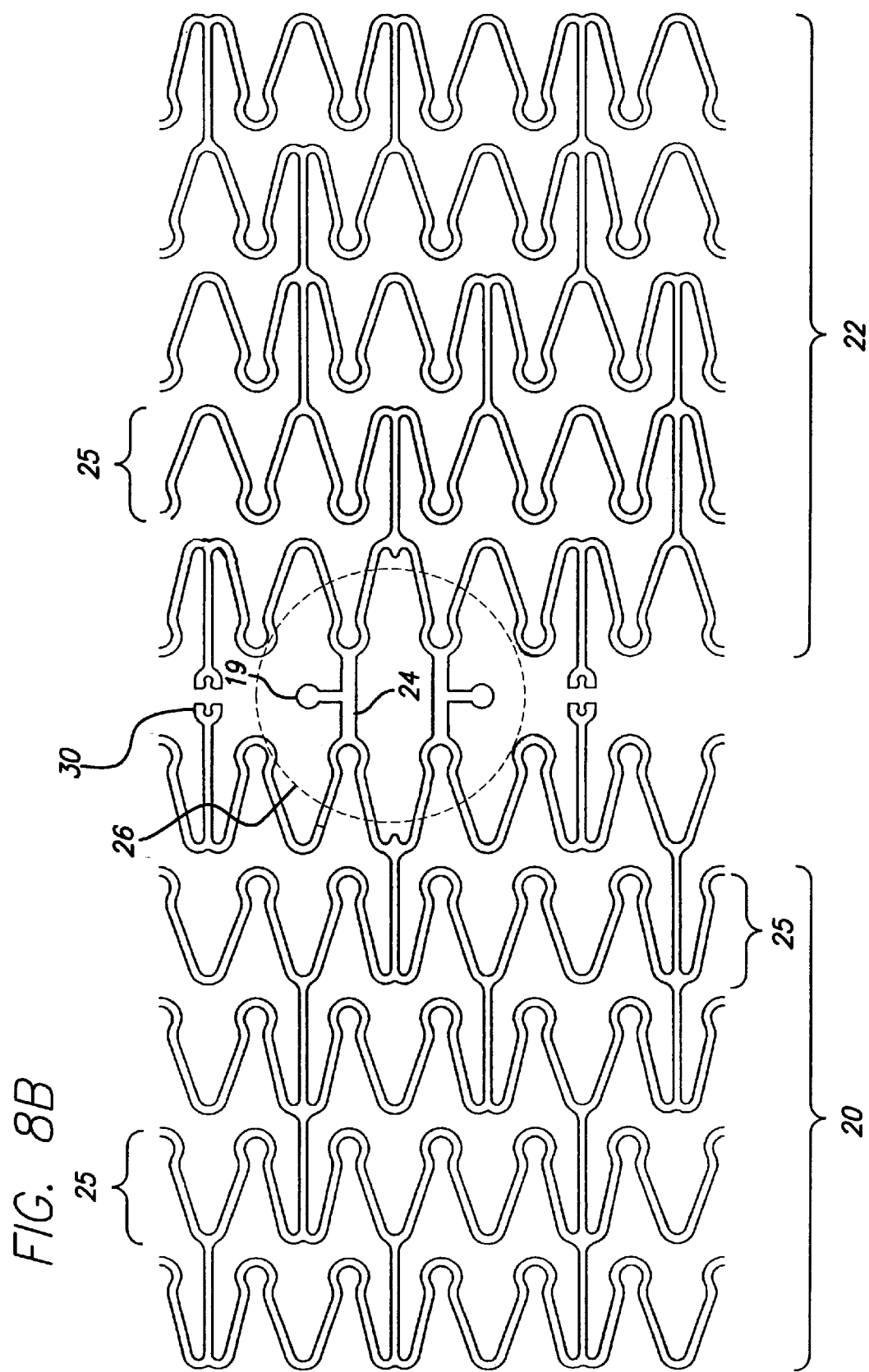
FIG. 8B is a plan view of the distal stent section carina junction and surrounding area of another embodiment of the Y-shaped stent of the present invention.

Turning now to FIGS. 8A and 8B, the structure of Y-shaped stent 14 is shown in greater detail at carina junction 26 of distal branches 20, 22. Preferably, the stent pattern of Y-shaped stent 14 is similar to that of U.S. Pat. No. 5,649,952 entitled "EXPANDABLE STENTS AND METHOD FOR MAKING SAME" and owned by Advanced Cardiovascular Systems, Incorporated, of Santa Clara, Calif., which is incorporated herein in its entirety by reference. The stent pattern of the Y-shaped stent also may be similar to that of any suitable stent design, including U.S. Pat. No. 5,514,154 entitled "EXPANDABLE STENTS" and owned by Advanced Cardiovascular Systems, Incorporated, of Santa Clara, California, which is incorporated herein in its entirety by reference. Other stent structures that could be used in conjunction with the Y-shaped stent of the present invention are also contemplated and are known in the art.

In another embodiment of the present invention, to aid in placement of the Y-shaped stent, cylindrical element 25 may be formed of a radiopaque biocompatible material selected from the group of materials including platinum-iridium, palladium-platinum-nickel, tantalum, or tantalum-titanium. The use of other suitable materials is contemplated as well. Further, radiopaque material may be applied to the carina junction or ends of the branches.

The carina junction 26 of the present invention serves at least three important functions. First, unlike some prior art bifurcated stents of the past, the carina junction of the present invention is designed such that sufficient scaffolding is present to entrap disease at the carina of a body lumen. Second, one or more bending elements 24 allow for the angle between the distal branches to be decreased. The bending elements also further aid in entrapping disease at the carina of a body lumen. Third, the carina junction, including the bending elements, facilitate proper placement of the Y-shaped stent at the carina of a body lumen. During delivery of the Y-shaped stent in a body lumen, the carina junction comes into apposition with the carina of the body lumen such that the Y-shaped stent can no longer be advanced distally. This facilitates precise placement of the Y-shaped stent. Some prior art devices were not physically connected at the carina junction of the stent, and this made it difficult for the physician to determine when the device came into apposition with the carina of the body lumen.

Referring to FIG. 8A, distal branches 20, 22 have one or more distal male struts 28 that assume a position to facilitate welding, as the angle between the distal branches is decreased. In an alternative embodiment, as depicted in FIG. 8B, the distal male struts, in this case lap joints 19, may be attached to bending elements 24 that are located proximate distal female struts 30. The lap joints bend outwardly, in a generally predictable fashion, as the angle between the distal branches is decreased. The distal branches may additionally have one or more distal female struts 30 that assume a position to facilitate welding, as the angle between the distal branches is decreased.

Figure 8C:
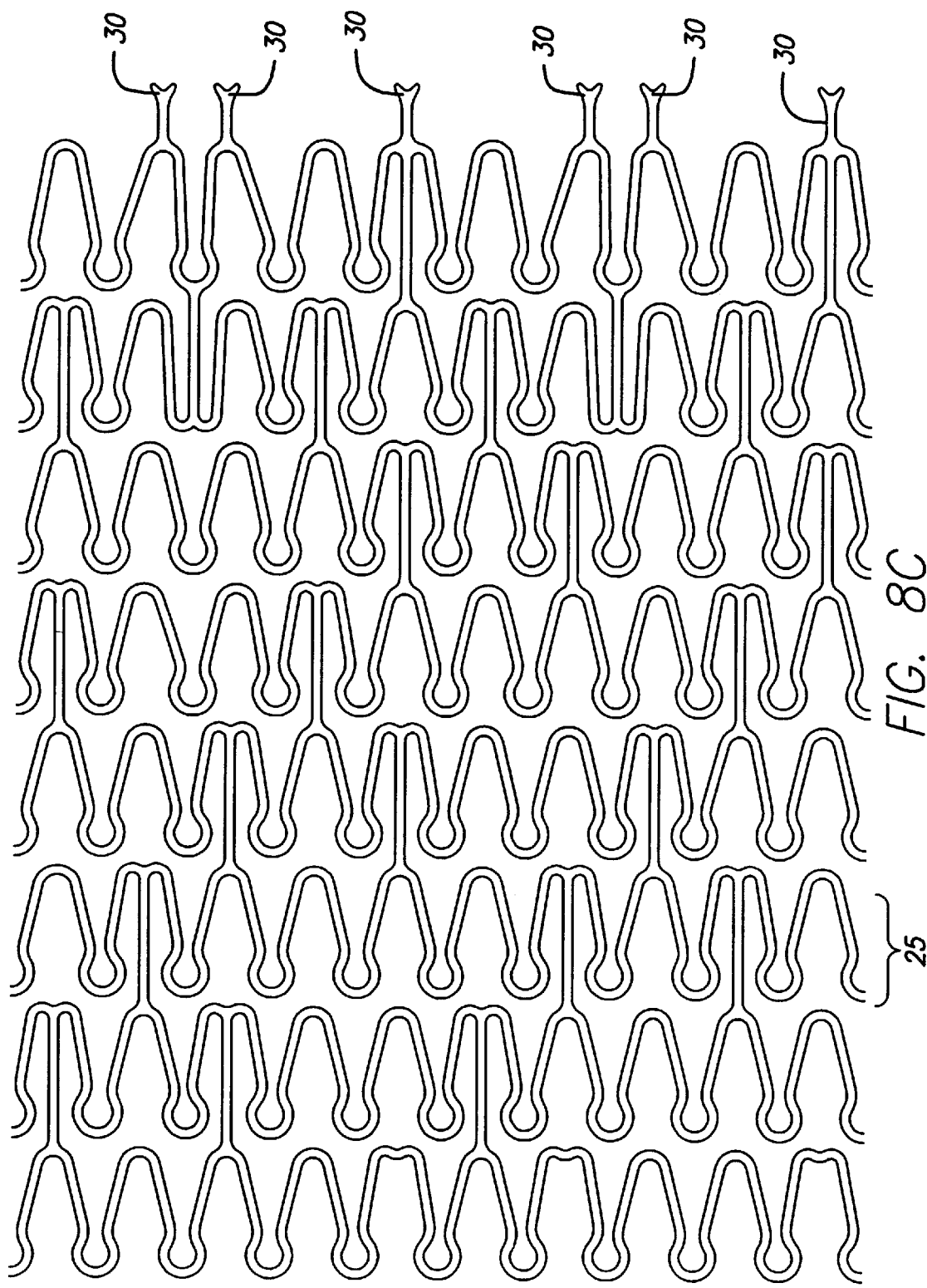
FIG. 8C is a plan view of a proximal stent section designed for mating with the distal stent section of FIG. 8A.
Figure 8D:
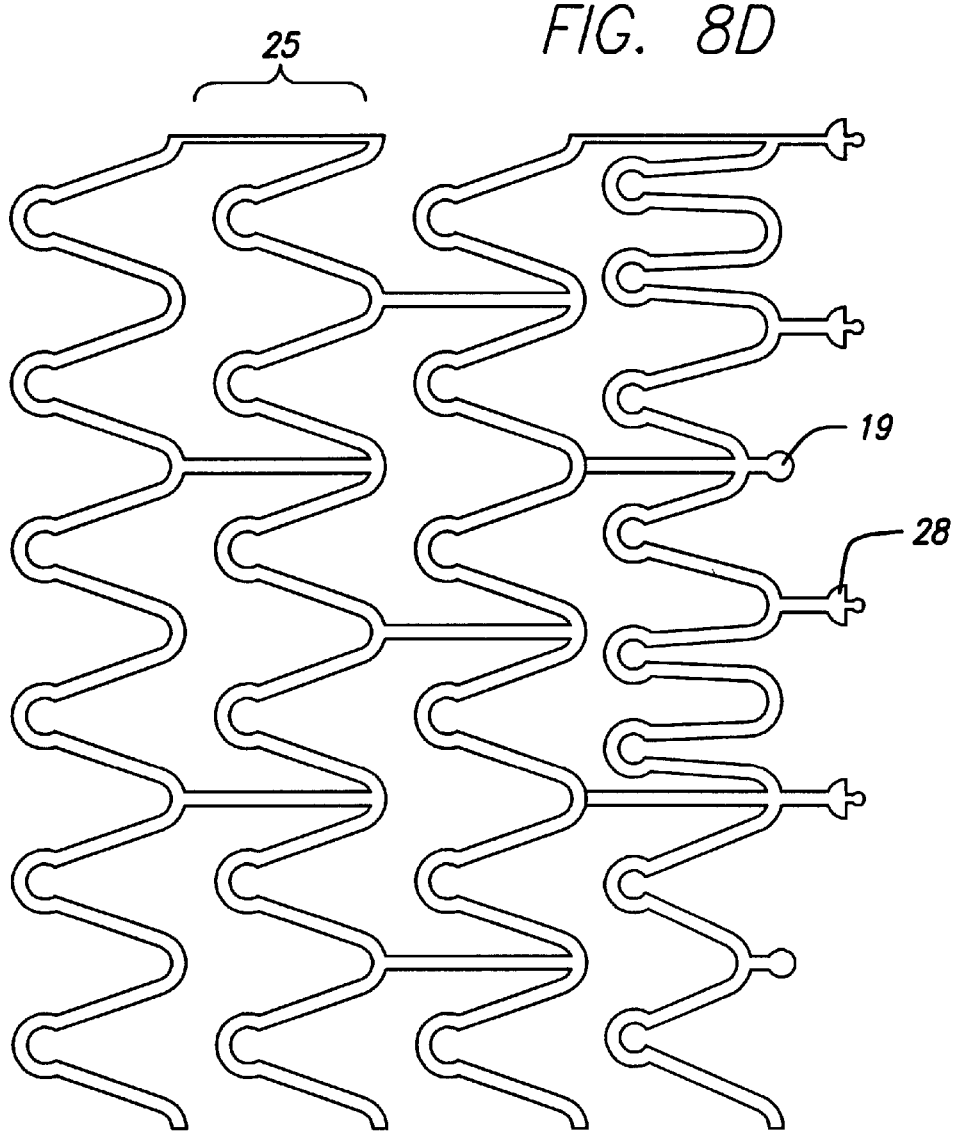
FIG. 8D is a plan view of a proximal stent section designed for mating with the distal stent section of FIG. 8B.

Turning to FIG. 8C, the proximal branch likewise has one or more proximal female struts 30. In an alternative embodiment, the proximal branch could additionally include one or more proximal male struts (not shown). The proximal male struts are designed to mate with the distal female struts and the proximal female struts are designed to mate with the distal male struts. FIG. 8D depicts a design of the proximal section that may be coupled with the distal section of FIG. 8B.

Figure 9A:
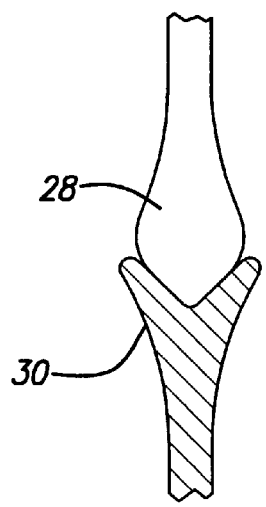
FIG. 9A is an elevational view, in section, of a male and a female strut in a first "fork," or "duck," configuration.
Figure 9E:
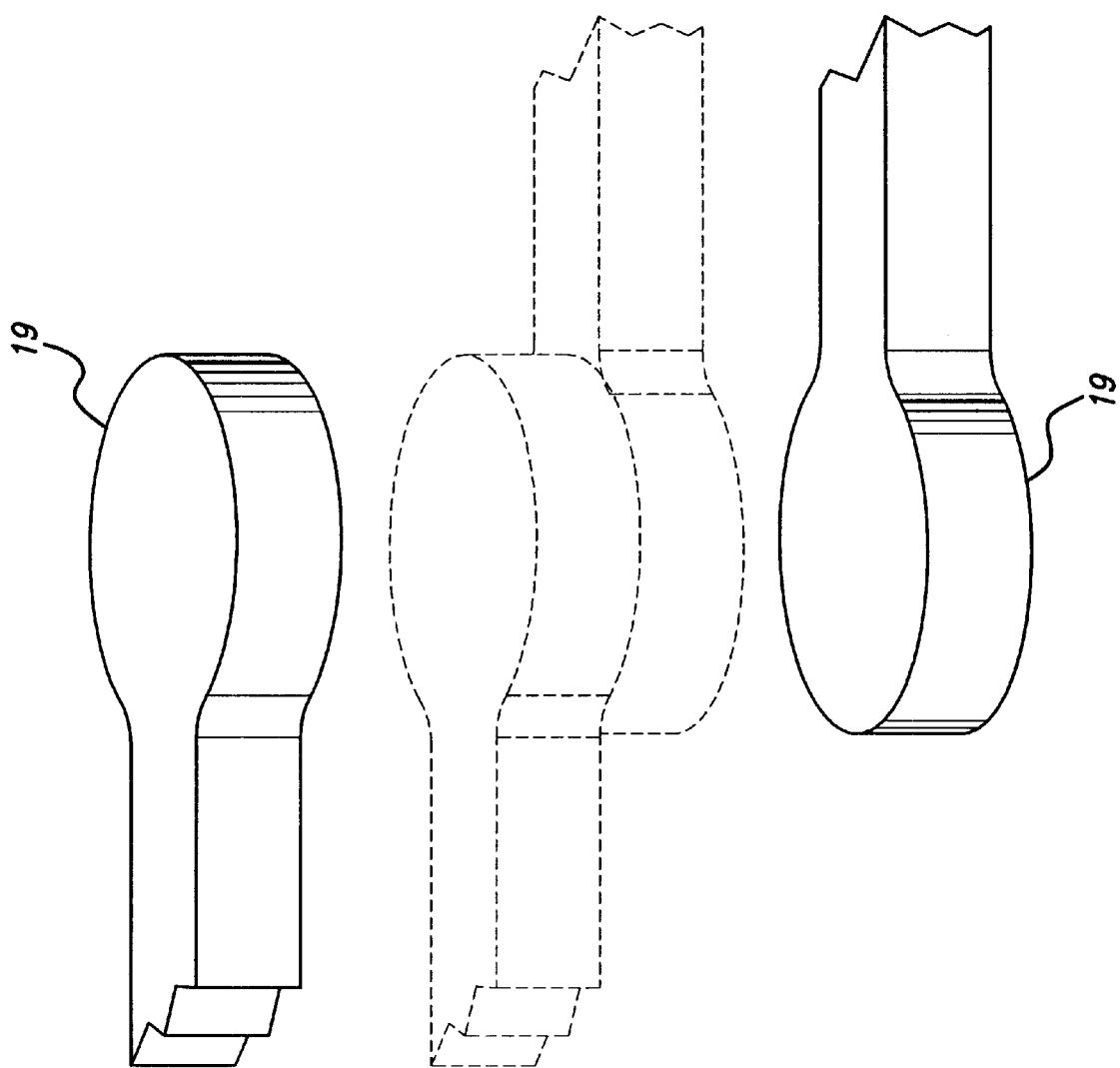
FIG. 9E is an elevational view, in section, of a "lap" joint.

Referring to FIGS. 9A–9E, the struts may be of various configurations. Preferably, as shown in FIG. 9A, male strut 28 and female strut 30 are preferably in a "fork," or "duck," configuration such that the male struts mechanically register with the female struts and cause alignment in at least one plane to facilitate laser welding or some other attachment method. FIG. 9B depicts a similar fork configuration. Turning to FIG. 9C, the male strut and the female strut are shown in a "locking butt," or "ball and socket," configuration. This configuration allows for the male struts to mechanically lock with the female struts to facilitate laser welding, or another form of attachment. Alternatively, as shown in FIG. 9D, the male strut and the female strut may be in a "butt" configuration. The strut of FIG. 9E is a "lap" joint 19 that may be laser welded or otherwise attached to a similar "lap" joint.

In one embodiment, Y-shaped stent 14 is formed from metal alloy tubing such as stainless steel tubing; however, the Y-shaped stent can be made from other biocompatible materials and metal alloys including, but not limited to, tantalum, nickel-titanium and its alloys, titanium and its alloys, platinum-iridium, chromium-cobalt, palladium-platinum-nickel, tantalum-titanium, platinum, and thermoplastic polymers. Additionally, the stent structure of the present invention may be coated with biocompatible coatings. Presently, one mode of making the Y-shaped stent is by direct laser cutting of stainless steel tubing as described in U.S. Pat. No. 5,759,192 entitled "METHOD AND APPARATUS FOR DIRECT LASER CUTTING OF METAL STENTS" and owned by Advanced Cardiovascular Systems, Incorporated, of Santa Clara, Calif., which is incorporated herein in its entirety by reference. Other modes of making the stent of the present invention, such as by chemical etching, are also contemplated and are known in the art.

Generally, a first metal tube and a second metal tube are supported for controlled linear and rotary motion. A finely focused laser beam is impinged upon the working surface of the first metal tube and the second metal tube. A protective mandrel is provided within the first tube and the second tube to protect the tube wall opposite the tube wall being cut from being ablated by the laser beam. A precise pattern is cut into the first tube to form proximal stent section 16 and a precise pattern is cut into the second tube to form distal stent section 18, the distal stent section having first generally cylindrical distal branch 20 and second generally cylindrical distal branch 22. The cutting is performed such that the first distal branch and the second distal branch, as previously described, are connected by bending elements 24 at carina junction 26. Likewise, the required male and female struts or lap joints are cut into the first tube and the second tube such that decreasing the angle between the distal branches serves to cause the male and female struts cut into the second tube to bend outwardly in a generally predictable fashion.

A descaling process is then performed after the laser cutting. The proximal stent section 16 and distal stent section 18 are placed into a diluted hydrochloric acid solution that reacts with the stainless steel and an oxide scale that has been formed through the laser cutting process. This breaks down the oxide scale. The stent sections are then placed into an ultrasonic bath of deionized water once the oxide scale is broken down. The ultrasonic bath aids in the removal of unwanted metal pieces known as islands. The stent sections are then inspected to ensure that all oxide and islands have been removed. Subsequently, the angle between the distal branches is decreased (FIG. 7C) such that the struts cut into the distal stent section assume a position to facilitate laser welding.

Figure 10B:
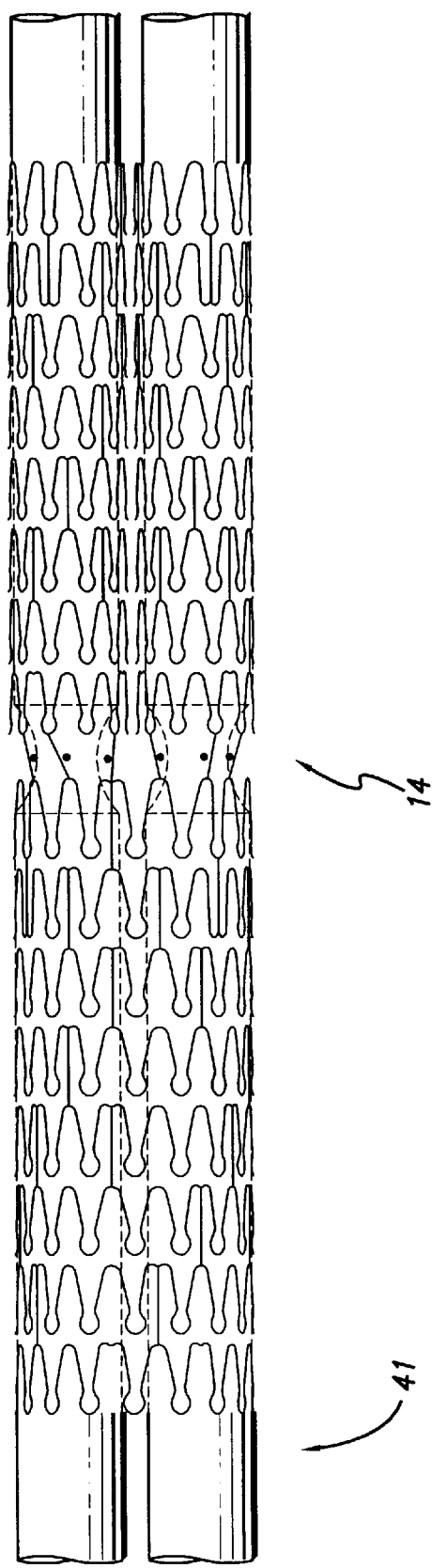
FIG. 10B is a perspective view of the welding mandrel after the Y-shaped stent is mounted thereon for welding.

Referring to FIGS. 10A and 10B, proximal stent section 16 and distal stent section 18 are then mounted on tapered welding mandrel 41. The welding mandrel is designed to cause the proximal stent section to flare out at its distal end so that male struts 28 can be mated with female struts 30. The male struts can then be laser welded to the female struts. Any lap joint present can also be welded to other lap joints. The last step in the fabrication process is a final inspection.

In another embodiment of the present invention, as depicted in FIGS. 11A–11C, Y-shaped stent 40 includes first stent section 42 having first main portion 44 and first hinged portion 46. The first hinged portion is hingedly attached to the first main portion such that the first stent section has an open configuration (shown in phantom in FIG. 11A) and a closed configuration. Second stent section 48 has second main portion 50 and second hinged portion 52. The second hinged portion is hingedly attached to the second main portion such that the second stent section has an open configuration (shown in phantom in FIG. 11B) and a closed configuration.

The first stent section 42 may be mated with second stent section 48 while the first stent section and the second stent section are in open configurations. Once mated, the first stent section together with the second stent section create a combination having a proximal end and a distal end in communication with each other. The proximal end includes generally cylindrical proximal branch 56. The distal end includes first generally cylindrical distal branch 58 and second generally cylindrical distal branch 60. The first and second distal branches and the proximal branch are structured so as to be in communication with each other. In one embodiment, the diameter of the proximal branch is matched to be approximately equal to the sum of the diameters of the distal branches. Thus, the proximal branch is designed to accommodate two balloons simultaneously, i.e., a "hugging balloon" technique, or one balloon and the proximal section of a second balloon simultaneously, i.e., a "kissing balloon" technique.

In another embodiment, Y-shaped stent 40 is expandable from a first smaller diameter for delivery in a body lumen to a second expanded diameter by plastically deforming the Y-shaped stent beyond the elastic limits of the material forming the stent. In another embodiment, the Y-shaped stent is formed from a self-expanding material so that the stent expands from a first smaller diameter for delivery through a body lumen to a second implanted diameter in the body lumen. The Y-shaped stent may be formed of a biocompatible material selected from the group of materials including stainless steel, tantalum, nickel-titanium and its alloys, titanium and its alloys, platinum-iridium, chromium-cobalt, palladium-platinum-nickel, tantalum-titanium, platinum, and thermoplastic polymers. The use of other suitable materials to form the Y-shaped stent is contemplated as well.

Typically, the proximal branch has an outer diameter on the order of about 0.075 inch (0.191 centimeter) to 0.115 in (0.292 cm) in the unexpanded condition, the same outer diameter of the hypotubing from which it is made, and can be expanded such that the inner diameter is approximately 0.16 in (4.0 mm) to 0.20 in (5.0 mm). The wall thickness of the proximal branch ranges from about 0.0015 in (0.0038 cm) to about 0.0065 in (0.0165 cm). The distal branch has an outer diameter on the order of about 0.045 in (0.114 cm) to 0.095 in (0.241 cm) in the unexpanded condition, the same outer diameter of the hypotubing from which it is made, and can be expanded such that the inner diameter is approximately 0.16 in (4.0 mm) to 0.20 in (5.0 mm). The wall thickness of the distal branches range from about 0.0015 in (0.0038 cm) to about 0.0065 in (0.0165 cm).

Preferably, the stent pattern of Y-shaped stent 40, as that of Y-shaped stent 14, is similar to that of U.S. Pat. No. 5,649,952 entitled "EXPANDABLE STENTS AND METHOD FOR MAKING SAME" and owned by Advanced Cardiovascular Systems, Incorporated, of Santa Clara, Calif., which is incorporated herein in its entirety by reference. However, the stent pattern of the Y-shaped stent may be also modeled after that of any suitable stent design, including U.S. Pat. No. 5,514,154 entitled "EXPANDABLE STENTS" and owned by Advanced Cardiovascular Systems, Incorporated, of Santa Clara, Calif., which is incorporated herein in its entirety by reference. Other stent structures that could be used in conjunction with the Y-shaped stent of the present invention are also contemplated and are known in the art.

In another embodiment of the present invention, to aid in placement of the Y-shaped stent, radiopaque biocompatible material may be applied to the carina junction or ends of the branches. The radiopaque material may be selected from the group of materials including platinum-iridium, palladium-platinum-nickel, tantalum, or tantalum-titanium. The use of other suitable materials is contemplated as well.

Turning again to FIGS. 11A and 11C, carina junction 62 may be used for placement. During delivery of Y-shaped stent 40 in a body lumen, the carina junction comes into apposition with the carina of the body lumen such that the Y-shaped stent can no longer be advanced distally. This facilitates precise placement of the Y-shaped stent. Thus, Y-shaped stent 40, like Y-shaped stent 14, solves the problem of some prior art devices that were not physically connected at the carina junction of the stent, thus making it difficult for the physician to determine when the device came into apposition with the carina of the body lumen.

The fabrication of Y-shaped stent 40 is similar in many respects to that of Y-shaped stent 14. In one embodiment, Y-shaped stent 40 is formed from metal alloy tubing such as stainless steel tubing; however, the Y-shaped stent can be made from other biocompatible materials and metal alloys including, but not limited to, tantalum, nickel-titanium and its alloys, titanium and its alloys, platinum-iridium, chromium-cobalt, palladium-platinum-nickel, tantalum-titanium, platinum, and thermoplastic polymers. Additionally, the stent structure of the present invention may be coated with biocompatible coatings.

Presently, one mode of making Y-shaped stent 40 is by direct laser cutting of stainless steel tubing as described in U.S. Pat. No. 5,759,192 entitled "METHOD AND APPARATUS FOR DIRECT LASER CUTTING OF METAL STENTS" and owned by Advanced Cardiovascular Systems, Incorporated, of Santa Clara, Calif. Other modes of making the stent of the present invention are also contemplated and are known in the art.

Generally, a first metal tube and a second metal tube are supported for controlled linear and rotary motion. A finely focused laser beam is impinged upon the working surface of the first metal tube and the second metal tube. A protective mandrel is provided within the first tube and the second tube to protect the tube wall opposite the tube wall being cut from being ablated by the laser beam. A precise pattern is cut into the first tube to form first stent section 42 having first main portion 44 and first hinged portion 46. The cutting is performed so that the first hinged portion is hingedly attached to the first main portion such that the first stent section has an open configuration and a closed configuration. A precise pattern is cut into the second tube to form second stent section 48 having second main portion 50 and second hinged portion 52. Likewise, the cutting is performed so that the second hinged portion is hingedly attached to the second main portion such that the second stent section has an open configuration and a closed configuration.

Next, the manufacturing steps are performed in a similar manner described above for Y-shaped stent 14. The first stent section 42 is attached to second stent section 48 while the two sections are in open configurations. Subsequently, the two sections are welded together in a similar manner as described above for Y-shaped stent 14.

A Y-shaped stent 60 of the present invention, which may include Y-shaped stent 14 or Y-shaped stent 40, can be implanted in the side-branch vessel to treat a number of angulated ostial lesions including, but not limited to, the following:

1. The ostium of a left anterior descending artery (LAD) where there is a circumflex or trifurcation vessel at less than 90° in its departure from the LAD.
2. The ostium of the circumflex artery or a trifurcation in a similar situation as number 1.
3. The ostium of a sizeable diagonal.
4. The LAD just distal to, but sparing, the origin of a diagonal.
5. The ostium of a circumflex marginal artery with an angulated take-off.

6. The ostium of a circumflex obtuse marginal artery with an angulated take-off.
7. Disease in the circumflex artery just distal to a marginal take-off, but sparing that take-off.
8. The aorta-ostium of a right coronary artery with an angled takeoff.
9. The left main bifurcation of the LAD and LCX.
10. The distal RCA-PDA (posterior descending artery) bifurcation.
11. The origin of an angulated posterior descending artery.
12. The origin of an LV extension branch just at and beyond the crux, sparing the posterior descending artery.
13. Any of many of the above locations in conjunction with involvement of the bifurcation and an alternate vessel.

When treating a bifurcation, the proper placement of the stent is critical. The present invention is suitable for treating lesions that standard stents cannot adequately treat. The treatment of bifurcated lesions with standard stents typically leads to sub-optimal results due to placement issues. If the stent is not precisely placed then the improper placement can lead to jailing of a vessel in the form of stent protrusion into the lumen or plaque protrusion due to an ostial gap. Improper stent placement can also lead to snowplowing the lesion. The necessary level of precision required to place a stent at a bifurcation is supplied by Y-shaped stent 60 because when advanced, the carina of the stent and the carina of the vessel are matched and the stent cannot be moved or placed more distal.

Figure 13:
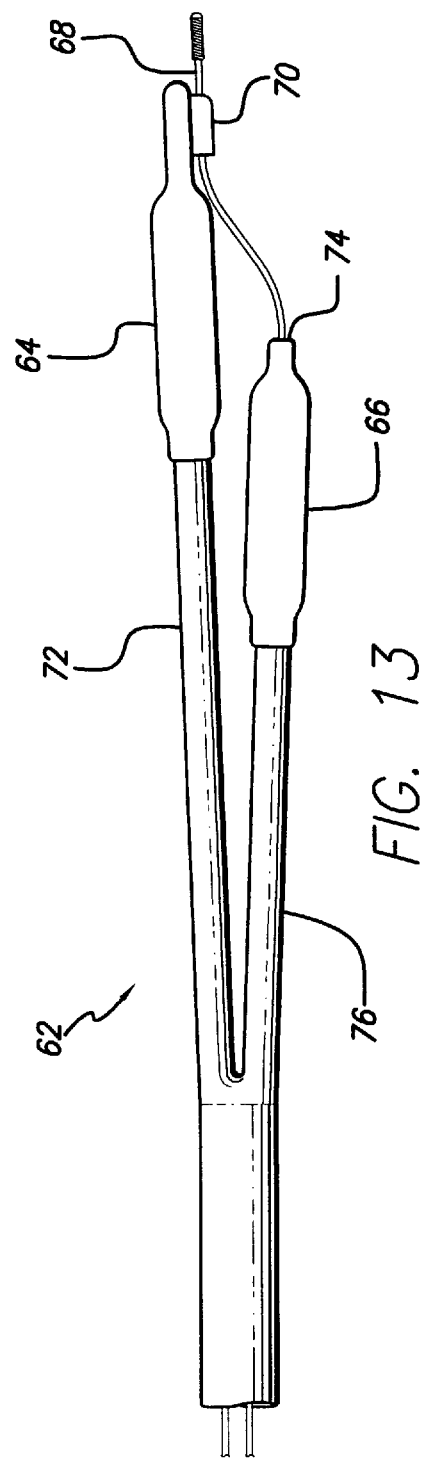
FIG. 13 is an elevational view of the bifurcated catheter assembly of FIG. 12 showing the catheter branches coupled together.
Figure 12:
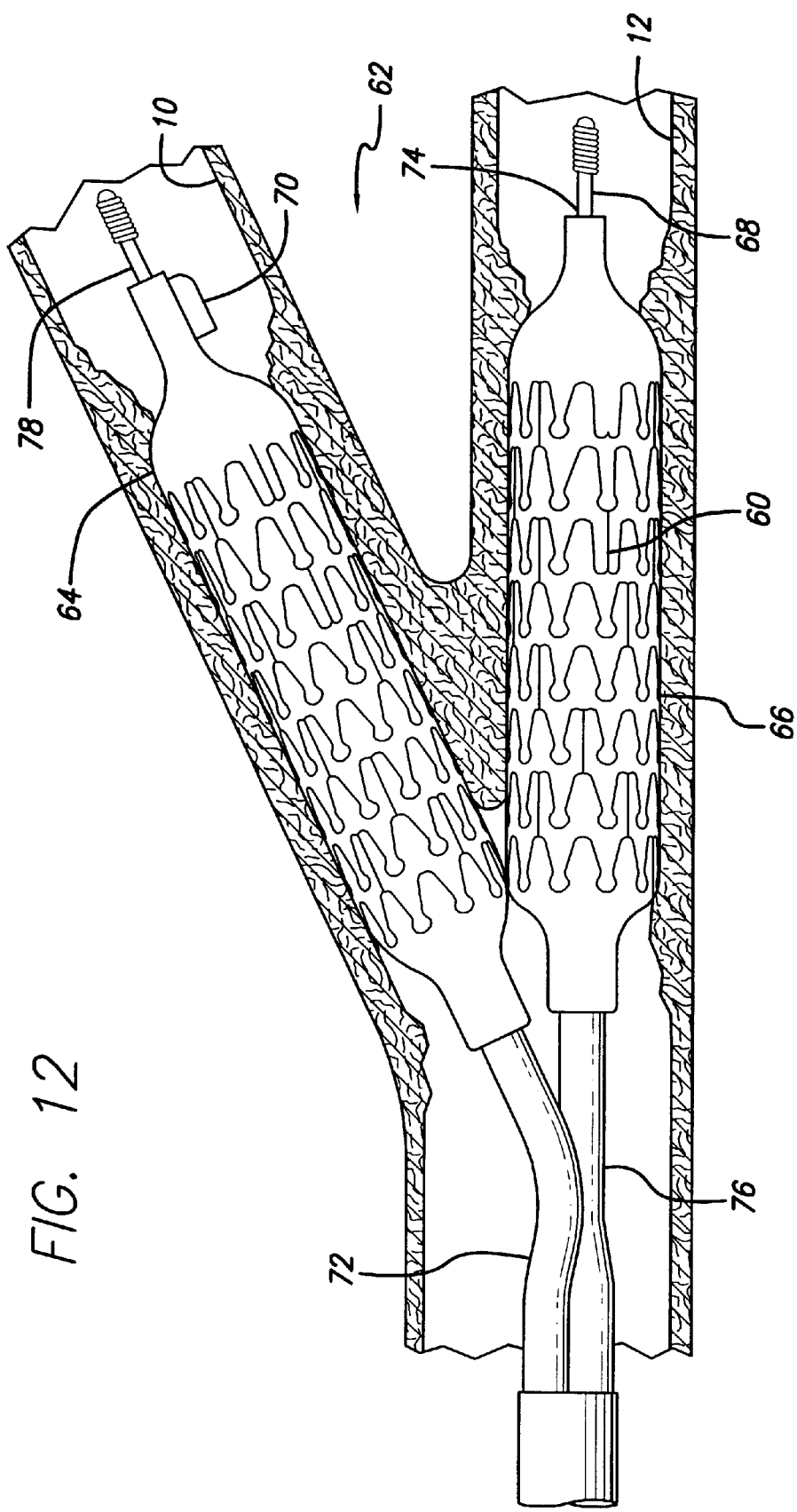
FIG. 12 is an elevational view, partially in section, showing a Y-shaped stent being deployed by a bifurcated catheter assembly.

Referring to FIGS. 12–13, in another embodiment, bifurcated catheter assembly 62 is used to deliver Y-shaped stent 60 to a damaged bifurcation in the body. The bifurcated catheter assembly is disclosed in U.S. patent application Ser. No. 09/138,844 entitled "BIFURCATED CATHETER ASSEMBLY" and filed Aug. 24, 1998, by Advanced Cardiovascular Systems, Incorporated, of Santa Clara, Calif., which is incorporated herein in its entirety by reference. In one embodiment, the bifurcated catheter assembly is of the rapid exchange type, which is known in the art.

The bifurcated catheter assembly 62 has Y-shaped stent 60 mounted on balloons 64, 66. A tracking guide wire 68 is inserted percutaneously into, for example, the femoral artery and is maneuvered to the bifurcation site such that the distal end of the tracking guide wire is in main vessel passage 12 distal to the bifurcation. Alternatively, the distal end of the tracking guide wire could be placed within side-branch vessel 10. The proximal end of the tracking guide wire is back-loaded proximally into the short tube of coupling device 70 located on catheter branch 72, as shown in FIG. 13. The distal end of the tracking guide wire is then further back-loaded proximally into distal tip 74 of catheter branch 76. The balloons 64, 66 are thus releasably held together. Passing the tracking guide wire through the tips of both branches allows for smooth, uninterrupted movement of the bifurcated catheter assembly to the target site.

In keeping with the invention, bifurcated catheter assembly 62 is then advanced over tracking guide wire 68 such that the balloons are in main vessel passage 12 proximate the bifurcation. The tracking guide wire is then withdrawn until its distal end exits the coupling device, thereby decoupling the balloons, as depicted in FIG. 12. The catheter assembly is then withdrawn until it passes the bifurcation with the tracking guide wire remaining in the main vessel. An integrated guide wire 78 is then advanced out of catheter branch 72 and into side-branch vessel 10. The catheter assembly is then advanced over both guide wires until the balloons and Y-shaped stent are anchored in the bifurcation. The balloons are inflated and the stent expanded and implanted in the bifurcation. It is also contemplated that two separate standard PTCA catheters can be used to deliver the stent. The catheters can be of equal length or of different lengths. Moreover, the two catheters can be separately inflated or can be simultaneously inflated, such as by utilization of a Y-connector.

Figure 14:
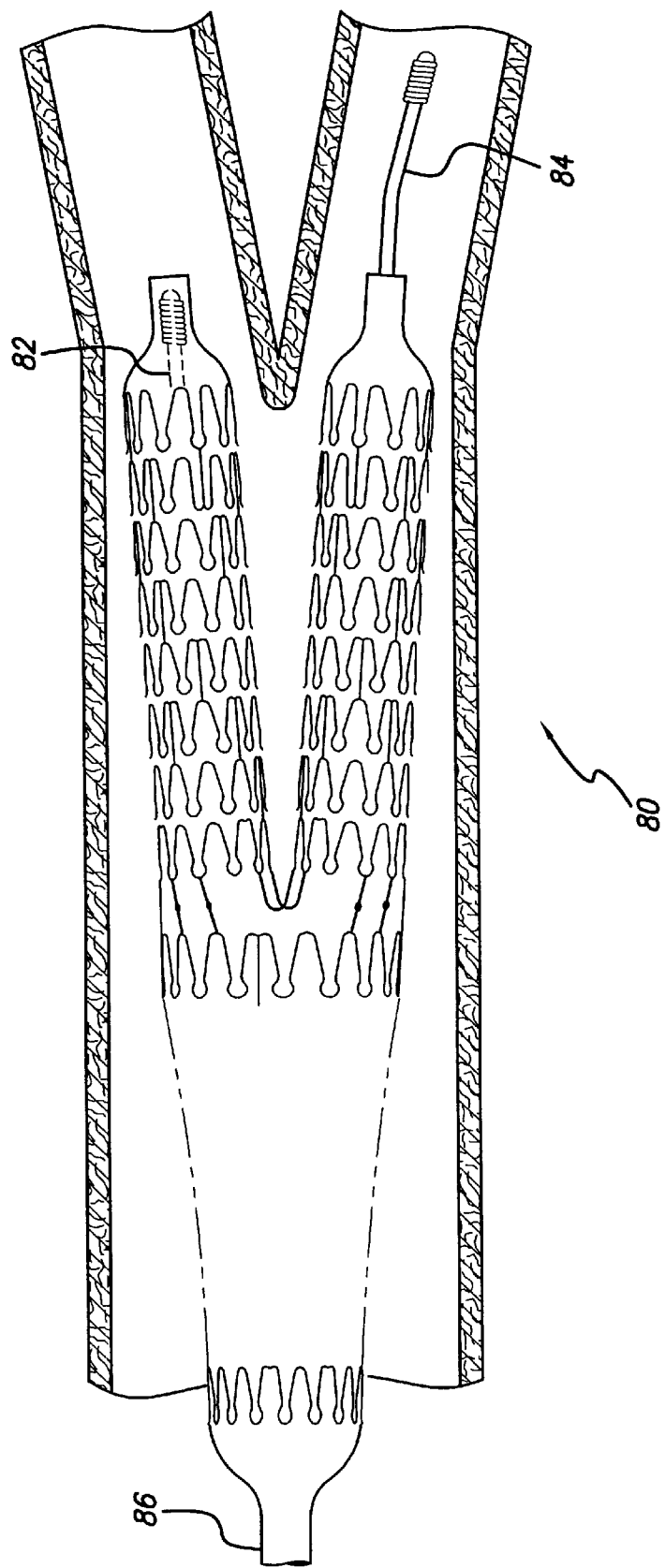
FIG. 14 is an elevational view, partially in section, showing a Y-shaped stent being deployed by a dual balloon Y-shaped catheter assembly.
Figure 15:
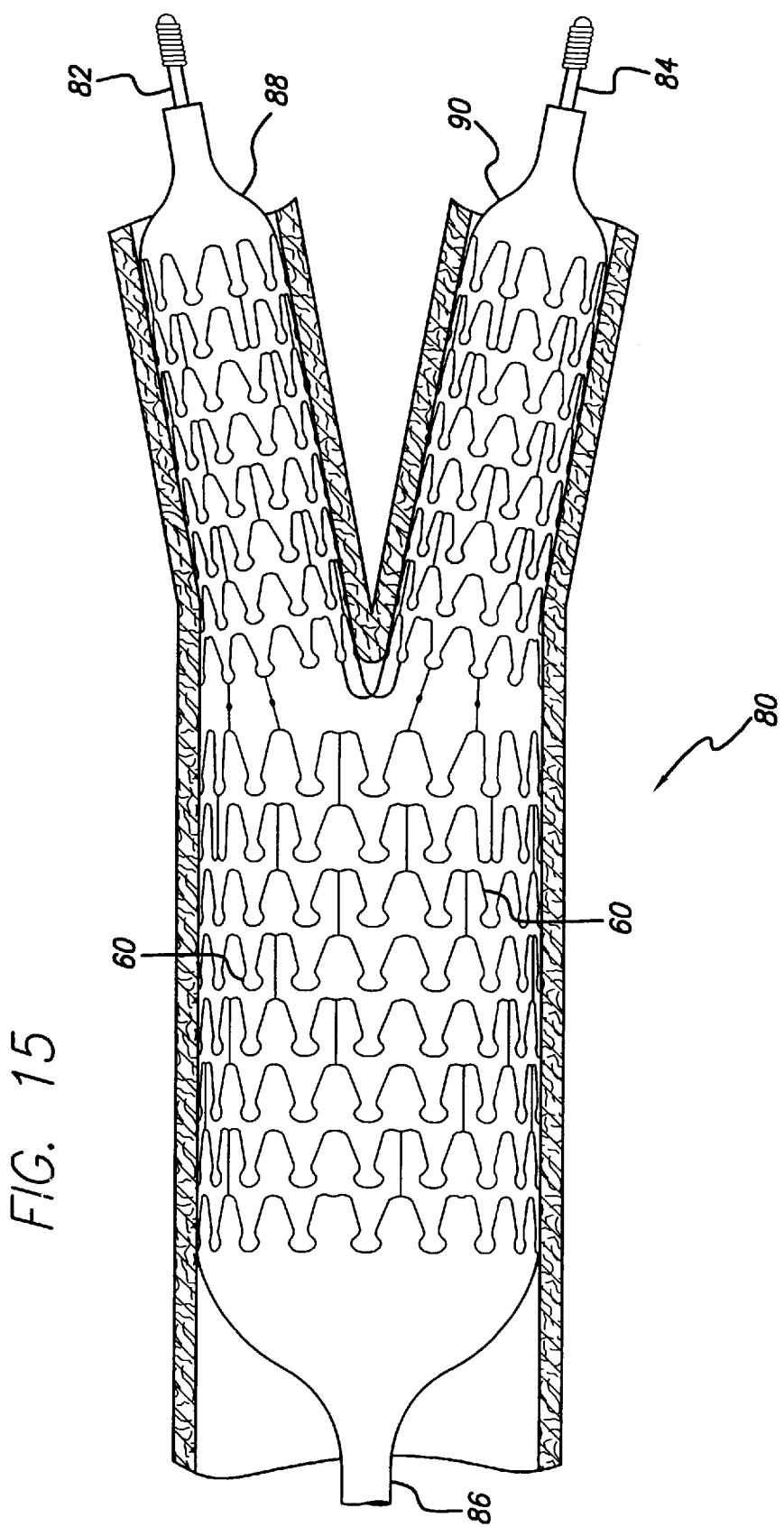
FIG. 15 is an elevational view, partially in section, showing a Y-shaped stent being deployed by a dual balloon Y-shaped catheter assembly.

In another embodiment as depicted in FIGS. 14 and 15, dual balloon Y-shaped catheter assembly 80 is used to deliver Y-shaped stent 60 to a damaged bifurcation in the body via guide wires 82, 84. Catheter 86 includes first and second expandable members 88, 90 that are configured to reside side by side (Y-shaped) for low profile delivery and to spring apart for implanting the stents. The Y-shaped stent is mounted on the first and second expandable members. The assembly is disclosed in U.S. patent application Ser. No. 08/910,857 entitled "STENT AND CATHETER ASSEMBLY AND METHOD FOR TREATING BIFURCATIONS" and filed Aug. 13, 1997, by Advanced Cardiovascular Systems, Incorporated, of Santa Clara, Calif., which is incorporated herein in its entirety by reference. Other assemblies that can be used to facilitate delivery of the Y-shaped stent of the present invention are also contemplated and are known in the art.

The dimensions and materials referenced herein are by way of example only and not intended to be limiting. Thus, for example, certain stent dimensions may vary to suit a particular application.

While the invention has been illustrated and described herein in terms of its use a Y-shaped stent for bifurcated vessels, it will be apparent to those skilled in the art that the invention can be used in other instances. Other modifications and improvements may be made without departing from the scope of the invention.

What is claimed is:
1. A longitudinally flexible Y-shaped stent for implanting in a bifurcated body lumen, comprising:
   a first generally cylindrical distal branch defined by a proximal end and a distal end and a series of expandable cylindrical elements which provide a first flow path for fluid flow;
   a second generally cylindrical distal branch defined by a proximal end and a distal end and a series of expandable cylindrical elements which provide a second flow path for fluid flow, wherein the first and second distal branches are interconnected by a plurality of bending elements that extend between cylindrical elements at the proximal end of each cylindrical branch to form a carina junction, each of the plurality of bending elements extending from the same cylindrical element within each cylindrical branch, and each of the bending elements being flexible such that the proximal end of the first and second distal branches are pivotally attached to the bending elements at the carina junction, thus defining an angle of varying degree such that the carina junction extends proximal the proximal end each distal branch; and
   a generally cylindrical proximal branch defining a third flow path for fluid flow, the proximal branch having a proximal end and a distal end and attached to the first and second distal branches proximal the carina junction such that the first and second distal branches and the proximal branch are in communication with each other, whereby during delivery of the Y-shaped stent in the bifurcated lumen the carina junction comes into appo- sition with the carina of the body lumen so that the Y-shaped stent can no longer be advanced distally, which facilitates precise placement of the Y-shaped stent in the bifurcated lumen.

2. The Y-shaped stent of claim 1, wherein sufficient scaffolding is present at the carina junction to entrap disease at the carina of the body lumen.

3. The Y-shaped stent of claim 1, wherein the Y-shaped stent is formed from a deformable material so that the stent is expandable from a first smaller diameter for delivery in a body lumen to a second expandable diameter by plastically deforming the Y-shaped stent beyond the elastic limits of the material forming the stent.

4. The Y-shaped stent of claim 1, wherein the Y-shaped stent is formed from a self-expanding material so that the stent self-expands from a first smaller diameter for delivery through a body lumen to a second implanted diameter in the body lumen.

5. The Y-shaped stent of claim 1, wherein the distal branches have one or more distal male struts that bend outwardly to facilitate attachment to the proximal branch, as the angle between the distal branches is decreased, and the proximal branch has one or more proximal female struts, wherein the proximal female struts male with the distal male struts.

6. The Y-shaped stent of claim 5, wherein the distal branches further have one or more distal female struts that bend outwardly to facilitate attachment to the proximal branch, as the angle between the distal branches is decreased, and the proximal branch further has one or more proximal male struts wherein the proximal male struts mate with the distal female struts.

7. The Y-shaped stent of claim 6, wherein the male struts mechanically register with female struts and cause alignment in at least one plane to facilitate attachment between the proximal branch and the distal branch.

8. The Y-shaped stent of claim 7, wherein the male struts can be attached to the female struts by laser welding.

9. The Y-shaped stent of claim 6, wherein the male struts mechanically lock with female struts, thereby facilitating attachment between the proximal branch and the distal branch.

10. The Y-shaped stent of claim 1, wherein the distal branches have one or more distal male or female struts that bend outwardly to facilitate attachment to the proximal branch, as the angle between the distal branches is decreased, and the proximal branch has one or more corresponding male or female struts, wherein the proximal struts mate with the distal struts.

11. The Y-shaped stent of claim 1, wherein the Y-shaped stent is formed from A biocompatible material selected from the group of materials including stainless steel, tantalum, nickel-titanium and its alloys, titanium and its alloys, platinum-iridium, chromium-cobalt, palladium-platinum-nickel, tantalum-titanium, platinum and thermoplastic polymers.

12. The Y-shaped stent of claim 1, wherein the diameter of the proximal branch is configured to be approximately equal to the sum of the diameter of the first distal branch and the diameter of the second distal branch.

13. A longitudinally flexible Y-shaped stent for implanting in a bifurcated body lumen, comprising:

a plurality of cylindrical elements that are independently expandable in the radial direction and that are interconnected so as to be generally aligned on a common longitudinal axis;

a plurality of connecting elements for interconnecting the cylindrical elements, the connecting elements configured to interconnect only the cylindrical elements that are adjacent to each other; and an outer wall surface on the cylindrical elements, the outer wall surface being smooth prior to expansion of the Y-shaped stent and forming a plurality of outwardly projecting edges that form as the stent is expanded radially outwardly from a first diameter to a second, enlarged diameter, wherein the Y-shaped stent has a proximal end and a distal end in communication with each other, the proximal end including a generally cylindrical proximal branch having a proximal end and a distal end and the distal end including a first generally cylindrical distal branch and a second generally cylindrical distal branch, the first distal branch and second distal branch defined by a proximal end and a distal end and a series of expandable cylindrical elements and pivotally attached to a plurality of bending elements that extend between cylindrical elements at the proximal end of each distal branch to form a carina junction, thus defining an angle of varying degree such that the carina junction extends proximal the proximal end of each distal branch, each of the plurality of bending elements extending from the same cylindrical element within each distal branch, and wherein the first and second distal branches are attached to the proximal branch proximal the carina junction.

14. A method of making an expandable metal Y-shaped stent, comprising the steps of:

providing a first metal tube;

providing a second metal tube;

forming a proximal stent section out of the first metal tube and a distal stent section out of the second metal tube, the distal stent section having a first distal branch and a second distal branch;

wherein the first distal branch and the second distal branch are connected by bending elements thereby forming a carina junction; and forming at least one of male struts and female struts in the first tube and at least one of male struts and female struts in the second tube such that decreasing the angle between the distal branches serves to cause the at least one of male struts and female struts formed in the second tube to bend outwardly to facilitate attachment of the first tube to the second tube, the male struts and female struts including one of a fork configuration, a ball and socket configuration, a butt configuration, and a lap joint configuration.

15. The method of claim 14, further comprising the steps of:

decreasing the angle between the distal branches such that the at least one of male struts and female struts formed in the second tube bend outwardly to facilitate welding of the first tube to the second tube;

attaching the proximal stent section to the distal stent section by mating the at least one of male struts and female struts in the first tube with the at least one of male struts and female struts in the second tube; and laser welding the male struts to the female struts.

* * * * *

UNITED STATES PATENT AND TRADEMARK OFFICE
CERTIFICATE OF CORRECTION

PATENT NO. : 6,673,107 B1
DATED : January 6, 2004
INVENTOR(S) : Brian D. Brandt, Joseph R. Callol and Hans F. Valencia It is certified that error appears in the above-identified patent and that said Letters Patent is hereby corrected as shown below:

Column 4,
Line 7, insert -- a -- after "from".

Column 7,
Line 55, delete "add" and insert -- and --.

Column 8,
Line 40, insert -- projecting -- before "edges".

Column 14,
Line 58, insert -- of -- after "end".

Column 15,
Line 11, delete "expandable" and insert -- expanded --.
Line 24, delete "male" and insert -- mate --.
Line 51, delete "A" and insert -- a --.

Signed and Sealed this

Sixth Day of July, 2004

JON W. DUDAS
*Acting Director of the United States Patent and Trademark Office*